US012738375B2

(12) United States Patent
Risher-Kelly

(10) Patent No.: US 12,738,375 B2
(45) Date of Patent: Sep. 15, 2026

(54) REMOTE VIEW DISTRIBUTION DEVICE IN A SERVICE-ORIENTED DEVICE CONNECTIVITY (SDC) NETWORK

(71) Applicant: Drägerwerk AG & Co. KGaA, Lübeck (DE)

(72) Inventor: Clifford Risher-Kelly, Wells, ME (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 725 days.

(21) Appl. No.: 18/081,812

(22) Filed: Dec. 15, 2022

(65) Prior Publication Data

US 2023/0197267 A1 Jun. 22, 2023

Related U.S. Application Data

(60) Provisional application No. 63/291,685, filed on Dec. 20, 2021.

(51) Int. Cl.

*G16H 40/67* (2018.01)
*G06F 3/14* (2006.01)
*H04L 67/12* (2022.01)

(52) U.S. Cl.

CPC ........... *G16H 40/67* (2018.01); *G06F 3/1454* (2013.01); *H04L 67/12* (2013.01)

(58) Field of Classification Search

CPC ........ G16H 40/67; G06F 3/1454; H04L 67/12
See application file for complete search history.

(56) References Cited

U.S. PATENT DOCUMENTS 8,273,018 B1 * 9/2012 Fackler .................. G08B 7/066 128/903
8,471,697 B2 * 6/2013 Judy .................... A61B 5/7425 340/539.12

(Continued)

FOREIGN PATENT DOCUMENTS

| | | | |
|---|---|---|---|
| CN | 116269210 | A | 6/2023 |
| EP | 3605550 | A1 | 2/2020 |
| EP | 4198710 | A1 | 6/2023 |

OTHER PUBLICATIONS

European Search Report for corresponding European Application No. 22213573.3; Dated May 8, 2023; 14 pages.

(Continued)

*Primary Examiner* — Blake J Rubin
(74) *Attorney, Agent, or Firm* — Nolte Lackenbach Siegel

(57) ABSTRACT

A method of distributing remote views in a point-to-point network includes: receiving first patient data corresponding to a first patient from a first physiological monitoring device via a first point-to-point connection; receiving second patient data corresponding to a second patient from a second physiological monitoring device via a second point-to-point connection; receiving a first medical data information base (MDIB) that includes the first patient data and a second MDIB that includes the second patient data, wherein the first MDIB comprises a plurality of first data objects and the second MDIB comprises a plurality of second data objects; selectively extracting at least one first data object from the first MDIB based on remote view configuration information; generating a first remote view MDIB comprising the extracted at least one first data object; and transmitting the first remote view MDIB to the second physiological monitoring device via the second point-to-point connection.

18 Claims, 17 Drawing Sheets

(56) References Cited

U.S. PATENT DOCUMENTS

| | | | | |
|---|---|---|---|---|
| 8,478,393 | B2 | 7/2013 | Ramanathan | |
| 8,645,164 | B2 | 2/2014 | Faiola | |
| 10,653,368 | B1 * | 5/2020 | McNair | A61B 5/021 |
| 12,343,142 | B2 * | 7/2025 | Muhsin | G16H 40/40 |
| 12,444,501 | B2 * | 10/2025 | Wang | G16H 80/00 |
| 2009/0171169 | A1 * | 7/2009 | Nagata | G16H 40/67 600/301 |
| 2009/0299150 | A1 * | 12/2009 | Alberte, Jr. | G16H 40/63 600/300 |
| 2011/0118561 | A1 * | 5/2011 | Tari | A61B 5/7445 600/301 |
| 2013/0267792 | A1 * | 10/2013 | Petersen | G16H 40/63 600/301 |
| 2013/0267873 | A1 | 10/2013 | Fuchs | |
| 2014/0135588 | A1 * | 5/2014 | Al-Ali | G16H 40/63 600/300 |
| 2016/0048636 | A1 | 2/2016 | Warner | |
| 2018/0020186 | A1 | 1/2018 | Gurmu | |
| 2018/0314801 | A1 * | 11/2018 | Janssen | G16H 40/63 |
| 2020/0204631 | A1 * | 6/2020 | Subramaniam | H04L 67/02 |
| 2022/0020491 | A1 * | 1/2022 | Martin | G16H 15/00 |
| 2022/0181020 | A1 * | 6/2022 | Keshavjee | A61B 5/1117 |
| 2022/0215948 | A1 * | 7/2022 | Bardot | G16H 40/40 |
| 2023/0111204 | A1 * | 4/2023 | Soni | A61M 16/026 726/7 |
| 2023/0162842 | A1 * | 5/2023 | Sudha | G16H 70/20 705/2 |
| 2023/0190208 | A1 * | 6/2023 | McSweeney | G06Q 10/06393 600/301 |
| 2023/0197267 | A1 | 6/2023 | Risher-Kelly | |
| 2023/0290511 | A1 * | 9/2023 | Kallonen | G06N 3/096 |
| 2025/0009292 | A1 * | 1/2025 | Izakson | A61N 1/0452 |

OTHER PUBLICATIONS

IEEE Standard, IEEE Piscataway, NJ, USA, Health Informatics-Point-Of_Care_Medical device Communication; Dated Jan. 15, 2019; pp. 1-45.

Mulet Niubo M .; "Designing a Communication Protocol for a Central Station Monitoring System"; Proceedings of the 25th Annual International Conference of the IEEE Engineering in Medicine and Biology Society (IEEE Cat No. 03CH37439). Cancun, Mexico, 2003, (Year 2003). 4 pages.

Rother Benjamin et al. "Automatic Configuration of a TSN Network for SDC-based Medical Device Networks" 2020 16th IEEE International Conference on Factory Communication System (WFCS), Porto, Portugal, 2020; 8 pages.

European Search Report for Corresponding EP Application No. 24209658.4; Dated Mar. 24, 2025; 10 pages.

* cited by examiner

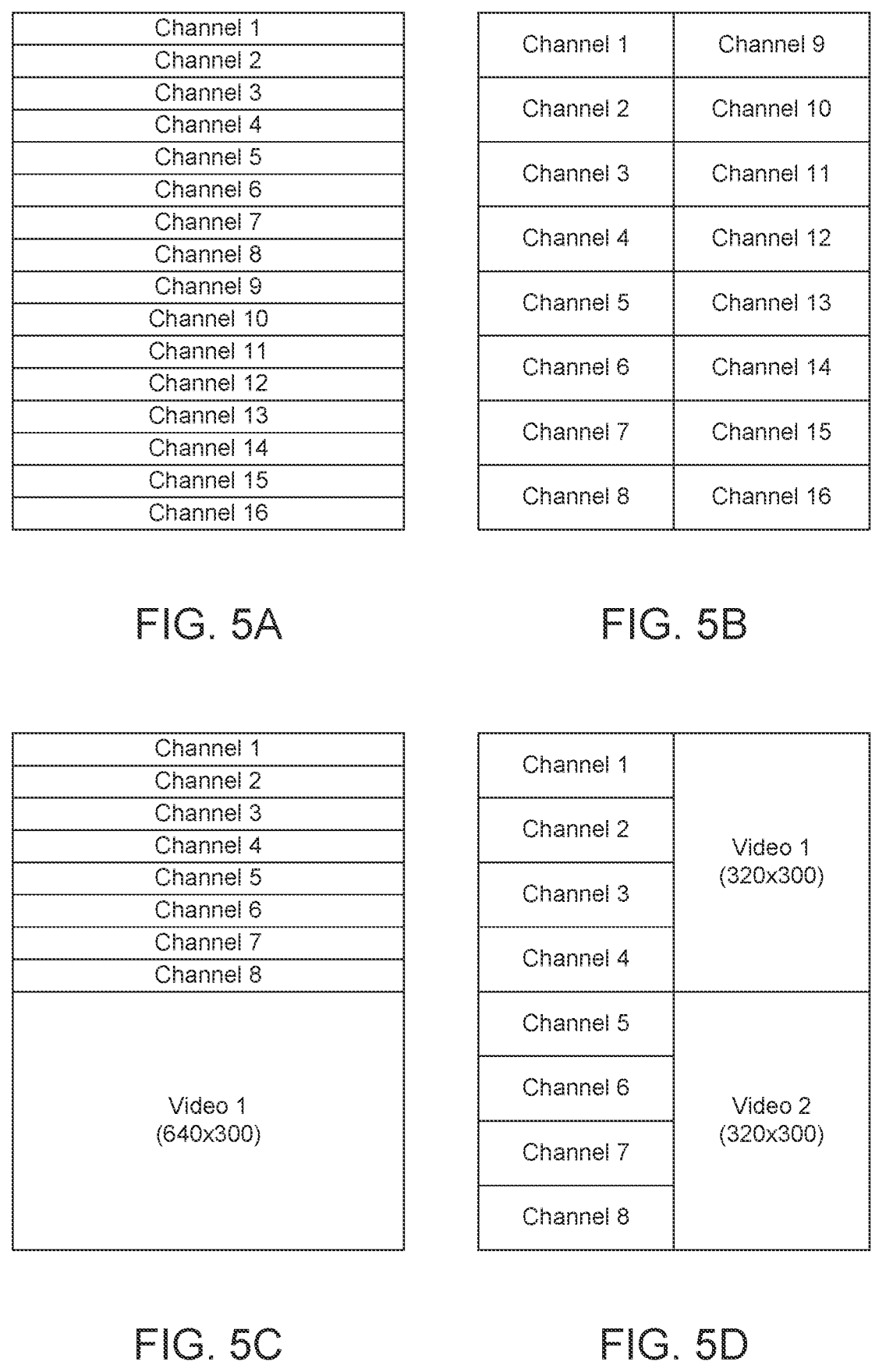

| Channel 1 |
| --- |
| Channel 2 |
| Channel 3 |
| Channel 4 |
| Channel 5 |
| Channel 6 |
| Channel 7 |
| Channel 8 |
| Channel 9 |
| Channel 10 |
| Channel 11 |
| Channel 12 |
| Channel 13 |
| Channel 14 |
| Channel 15 |
| Channel 16 |

FIG. 5A

| Channel 1 | Channel 9 |
| --- | --- |
| Channel 2 | Channel 10 |
| Channel 3 | Channel 11 |
| Channel 4 | Channel 12 |
| Channel 5 | Channel 13 |
| Channel 6 | Channel 14 |
| Channel 7 | Channel 15 |
| Channel 8 | Channel 16 |

FIG. 5B

| Channel 1 |
| --- |
| Channel 2 |
| Channel 3 |
| Channel 4 |
| Channel 5 |
| Channel 6 |
| Channel 7 |
| Channel 8 |
| Video 1 (640x300) |

FIG. 5C

| Channel 1 | Video 1 (320x300) |
| --- | --- |
| Channel 2 | |
| Channel 3 | |
| Channel 4 | |
| Channel 5 | Video 2 (320x300) |
| Channel 6 | |
| Channel 7 | |
| Channel 8 | |

FIG. 5D

REMOTE VIEW DISTRIBUTION DEVICE IN A SERVICE-ORIENTED DEVICE CONNECTIVITY (SDC) NETWORK

BACKGROUND

Patient monitors are devices that are configured to receive physiological data from another device and either display a patient's physiological data, monitor a patient's physiological data, or both. A patient monitor may be configured to be worn by a patient, may be a hand-held device, may be docked to or undocked from a larger unit such as a monitor mount, and, thus, may be transportable. For example, a monitor mount may be a larger patient monitor or a console that has a docking interface or docking receptacle to which the patient monitor can be removably docked.

Some patient monitors both support a local view and a remote view on a display. A local view pertains to displaying a physiological data of a patient that is located locally with respect to the patient monitor. In other words, in a local view, a patient monitor displays physiological data obtained by sensors, medical devices, and/or therapy devices that interface with a local patient. The patient monitor itself is located proximate to the local patient (e.g., in the same room or bedside) and can be said to be assigned to the local patient. In contrast, a remote view pertains to displaying a physiological data of a patient that is located remote with respect to the patient monitor. In other words, physiological data of a remote patient is obtained from a different, remote patient monitor and the patient monitor may be located remote from a remote patient (e.g., in a different room or bedside). Thus, a remote view enables a clinician to view a visual representation of another patient monitor on a local patient monitor.

A patient monitor that supports both local and remote views can display physiological data of a local patient and of one or more remote patients by, for example, a split screen, screen overlays, and the like, with each portion of a screen dedicated to a different patient.

A patient monitor may be configured into an Actionable Bed-to-Bed Alarm mode for providing a remote view of another patient monitor. Because a patient monitor is often assigned to a bed, and thus to a specific patient residing in that bed, a patient monitor may be referred to as a "bed". A bed may be used as a generic term for a ventilator machine, an anesthesia machine, or any other device that is assigned to a specific local location or patient. A patient monitor configured into Actionable Bed-to-Bed Alarm mode is configured to provide an alarm generated by a remote patient monitor to a clinician in real-time so that the clinician can determine if an emergency situation is occurring at a remote bed (i.e., at a remote patient monitor and specifically at a remote patient). In this case, the latency of the connection between patient monitors and displaying or rendering the physiological data of the remote patient on the screen of the local patient monitor is critical to the function.

In past generations of patient monitors, multi-cast was used on the network as a means for each monitor to broadcast their waveforms and parameters to all consumers on the network. This multi-cast communication included connections to a central station, a gateway, and other patient monitors that were configured for remote viewing of this data. With the new communication standard of service-oriented device connectivity (SDC), multicast is not permitted due to security reasons and all data must be sent with point-to-point connections. Multicast is group communication where data transmission is addressed to a group of destination computers simultaneously. In contrast, SDC is a web services-based architecture that enables interoperability amongst point-of-care medical devices and data exchange between point-of-care devices and Health Level Seven (HL7) compatible clinical and hospital information systems. In other words, SDC provides separate point-to-point connections to each device. It enables a hospital's medical technologies to share data and information bi-directionally, securely, and dynamically.

The process of making an SDC connection and generating waveforms and alarms on the screen using the platform software is too slow for the Actionable Bed-to-Bed Alarm functionality. In addition, supporting the possible number of SDC connections required for a care group is not feasible with the present CPU power of a patient monitor. Therefore, a device capable of providing a remote view cluster service that supports SDC connections between devices with low latency may be desired.

SUMMARY

In some aspects, the techniques described herein relate to a remote view distribution device, including: a first service-oriented device connectivity (SDC) connection interface configured to be connected to a first physiological monitoring device for receiving first patient data corresponding to a first patient; a second SDC connection interface configured to be connected to a second physiological monitoring device for receiving second patient data corresponding to a second patient; a medical data information base (MDIB) buffer configured to receive a first MDIB that includes the first patient data and a second MDIB that includes the second patient data, wherein the first MDIB includes a plurality of first data objects and the second MDIB includes a plurality of second data objects; and a processing circuit configured to selectively extract at least one first data object from the first MDIB based on remote view configuration information, generate a first remote view MDIB including the extracted at least one first data object, and transmit the first remote view MDIB to the second physiological monitoring device via the second SDC connection interface.

In some aspects, the techniques described herein relate to a remote view distribution device, wherein the processing circuit is configured to selectively extract at least one second data object from the second MDIB based on the remote view configuration information, generate a second remote view MDIB including the extracted at least one second data object, and transmit the second remote view MDIB to the first physiological monitoring device via the first SDC connection interface.

In some aspects, the techniques described herein relate to a remote view distribution device, further including: a synchronizer configured to receive the first MDIB and the second MDIB from the MDIB buffer and synchronize transmissions of the first MDIB and the second MDIB to the processing circuit.

In some aspects, the techniques described herein relate to a remote view distribution device, wherein the remote view configuration information includes configuration information received from the first physiological monitoring device and configuration information received from the second physiological monitoring device.

In some aspects, the techniques described herein relate to a remote view distribution device, further including: a third SDC connection interface configured to be connected to a third physiological monitoring device for receiving third patient data corresponding to a third patient, wherein the MDIB buffer is configured to receive a third MDIB that includes the third patient data, wherein the third MDIB includes a plurality of third data objects, and wherein the processing circuit is configured to selectively extract at least one third data object from the third MDIB based on the remote view configuration information, generate the first remote view MDIB including the extracted at least one first data object and the extracted at least one third data object, and transmit the first remote view MDIB to the second physiological monitoring device via the second SDC connection interface.

In some aspects, the techniques described herein relate to a remote view distribution device, further including: a third SDC connection interface configured to be connected to a third physiological monitoring device for receiving third patient data corresponding to a third patient, wherein the MDIB buffer is configured to receive a third MDIB that includes the third patient data, wherein the third MDIB includes a plurality of third data objects wherein the processing circuit is configured to generate a second remote view MDIB including the extracted at least one first data object, and transmit the second remote view MDIB to the third physiological monitoring device via the third SDC connection interface.

In some aspects, the techniques described herein relate to a remote view distribution device, further including: a third SDC connection interface configured to be connected to a third physiological monitoring device for receiving third patient data corresponding to a third patient, wherein the MDIB buffer is configured to receive a third MDIB that includes the third patient data, wherein the third MDIB includes a plurality of third data objects wherein the processing circuit is configured to selectively extract a first data portion of the plurality of first data objects from the first MDIB based on the remote view configuration information for the first remote view MDIB, extract a second data portion of the plurality of first data objects from the first MDIB based on the remote view configuration information for a second remote view MDIB, wherein the first and the second data portions are different data portions, generate the first remote view MDIB including the extracted first data portion, generate the second remote view MDIB including the extracted second data portion, transmit the first remote view MDIB to the second physiological monitoring device via the second SDC connection interface, and transmit the second remote view MDIB to the third physiological monitoring device via the third SDC connection interface.

In some aspects, the techniques described herein relate to a remote view distribution device, wherein the first remote view MDIB is configured to enable the second physiological monitoring device to render a remote view on a display.

In some aspects, the techniques described herein relate to a remote view distribution device, including: a plurality of service-oriented device connectivity (SDC) connection interfaces each configured to be connected to a respective physiological monitoring device of a plurality physiological monitoring devices for receiving patient data from each of the plurality physiological monitoring devices; a medical data information base (MDIB) buffer configured to receive a plurality of MDIBs, including receiving a corresponding MDIB for each of the plurality physiological monitoring devices that includes the patient data received from a respective physiological monitoring device, wherein each corresponding MDIB includes a plurality of data objects; and a processing circuit configured to: generate a remote view MDIB based on remote view configuration information, including selectively extracting at least one data object from the plurality of MDIBs and generating the remote view MDIB including the extracted at least one data object, and transmit the remote view MDIB to at least one physiological monitoring device of the plurality physiological monitoring devices via a respective one or more SDC connection interfaces based on the remote view configuration information.

In some aspects, the techniques described herein relate to a remote view distribution device, wherein the remote view configuration information identifies the at least one data object to be extracted from the plurality of MDIBs and identifies the at least one physiological monitoring device to which the remote view MDIB is to be transmitted.

In some aspects, the techniques described herein relate to a remote view distribution device, further including: a synchronizer configured to receive the plurality of MDIBs from the MDIB buffer and synchronize transmissions of the plurality of MDIBs to the processing circuit.

In some aspects, the techniques described herein relate to a remote view distribution device, wherein the remote view MDIB is configured to enable the at least one physiological monitoring device to render a remote view on a display.

In some aspects, the techniques described herein relate to a remote view distribution device, including: a first service-oriented device connectivity (SDC) connection interface configured to be connected to a first physiological monitoring device for receiving first patient data corresponding to a first patient; a second SDC connection interface configured to be connected to a physiological monitoring device for receiving second patient data corresponding to a first patient; a data block buffer configured to receive a first data block that includes the first patient data and a second data block that includes the second patient data, wherein the first data block includes a plurality of first data objects and the second data block includes a plurality of second data objects; and a processing circuit configured to selectively extract at least one first data object from the first data block based on remote view configuration information, generate a first remote view data block including the extracted at least one first data object, and transmit the first remote view data block to the second physiological monitoring device via the second SDC connection interface.

In some aspects, the techniques described herein relate to a remote view distribution system, including: a plurality of physiological monitoring devices, each configured to monitor one or more physiological parameters of a respective patient and each including a display configured to display a local view of its respective patient and a remote view of at least one remote patient; a plurality of service-oriented device connectivity (SDC) connections, each connected to a different one of the plurality of physiological monitoring devices; and a remote view distribution device connected to the plurality of SDC connections for receiving patient data from each of the plurality physiological monitoring devices, wherein the remote view distribution device includes: a medical data information base (MDIB) buffer configured to receive a plurality of MDIBs, including receiving a corresponding MDIB for each of the plurality physiological monitoring devices that includes the patient data received from a respective physiological monitoring device, wherein each corresponding MDIB includes a plurality of data objects; and a processing circuit configured to: generate a remote view MDIB based on remote view configuration information, including selectively extracting at least one data object from the plurality of MDIBs and generating the remote view MDIB including the extracted at least one data object, and transmit the remote view MDIB to at least one physiological monitoring device of the plurality physiological monitoring devices via a respective one or more SDC connections based on the remote view configuration information.

In some aspects, the techniques described herein relate to a remote view distribution system, wherein the remote view configuration information identifies the at least one data object to be extracted from the plurality of MDIBs and identifies the at least one physiological monitoring device to which the remote view MDIB is to be transmitted.

In some aspects, the techniques described herein relate to a remote view distribution system, further including: a synchronizer configured to receive the plurality of MDIBs from the MDIB buffer and synchronize transmissions of the plurality of MDIBs to the processing circuit.

In some aspects, the techniques described herein relate to a remote view distribution system, wherein the remote view MDIB is configured to enable the at least one physiological monitoring device to render a respective remote view on its display.

In some aspects, the techniques described herein relate to a remote view distribution system, further including: a data source configured to provide additional patient information with respect a patient, wherein the processing circuit is configured to receive the additional patient information and insert the additional patient information into the remote view MDIB. The data source may be a camera and the additional patient information may be a video stream of the patient.

In some aspects, the techniques described herein relate to a remote view distribution device, including: a first point-to-point connection interface configured to be connected to a first physiological monitoring device for receiving first patient data corresponding to a first patient; a second point-to-point connection interface configured to be connected to a second physiological monitoring device for receiving second patient data corresponding to a second patient; a medical data information base (MDIB) buffer configured to receive a first MDIB that includes the first patient data and a second MDIB that includes the second patient data, wherein the first MDIB includes a plurality of first data objects and the second MDIB includes a plurality of second data objects; and a processing circuit configured to selectively extract at least one first data object from the first MDIB based on remote view configuration information, generate a first remote view MDIB including the extracted at least one first data object, and transmit the first remote view MDIB to the second physiological monitoring device via the second point-to-point connection interface.

In some aspects, the techniques described herein relate to a remote view distribution system arranged in a point-to-point network, including: a plurality of physiological monitoring devices, each configured to monitor one or more physiological parameters of a respective patient and each including a display configured to display a local view of its respective patient and a remote view of at least one remote patient; a plurality of point-to-point connections, each connected to a different one of the plurality of physiological monitoring devices; and a remote view distribution device connected to the plurality of point-to-point connections for receiving patient data from each of the plurality physiological monitoring devices, wherein the remote view distribution device includes: a data block buffer configured to receive a plurality of data blocks, including receiving a corresponding data block for each of the plurality physiological monitoring devices that includes the patient data received from a respective physiological monitoring device, wherein each corresponding data block includes a plurality of data objects; and a processing circuit configured to: generate a remote view data block based on remote view configuration information, including selectively extracting at least one data object from the plurality of data blocks and generating the remote view data block including the extracted at least one data object, and transmit the remote view data block to at least one physiological monitoring device of the plurality physiological monitoring devices via a respective one or more point-to-point connections based on the remote view configuration information.

In some aspects, the techniques described herein relate to a method of distributing remote views in a point-to-point network, the method including: receiving a first medical data information base (MDIB) that includes first patient data corresponding to a first patient from a first physiological monitoring device via a first point-to-point connection, wherein the first MDIB comprises a plurality of first data objects; receiving a second MDIB that includes second patient data corresponding to a second patient from a second physiological monitoring device via a second point-to-point connection, wherein the second MDIB comprises a plurality of second data objects; selectively extracting at least one first data object from the first MDIB based on remote view configuration information; generating a first remote view MDIB including the extracted at least one first data object; and transmitting the first remote view MDIB to the second physiological monitoring device via the second point-to-point connection.

BRIEF DESCRIPTION OF THE DRAWINGS

In the drawings, like reference numbers generally indicate identical, functionally similar, and/or structurally similar elements.

FIG. 5A shows a first format of output buffers of the remote view distribution device that comprises 16 vertical channels;

FIG. 5B shows a second format of output buffers of the remote view distribution device that comprises 8 vertical channels with two channels side-by-side;

FIGS. 5C and 5D show additional formats of output buffers if compressed video is used. The video format would allow mixing of video and patient monitoring data.

DETAILED DESCRIPTION

Figure 1:
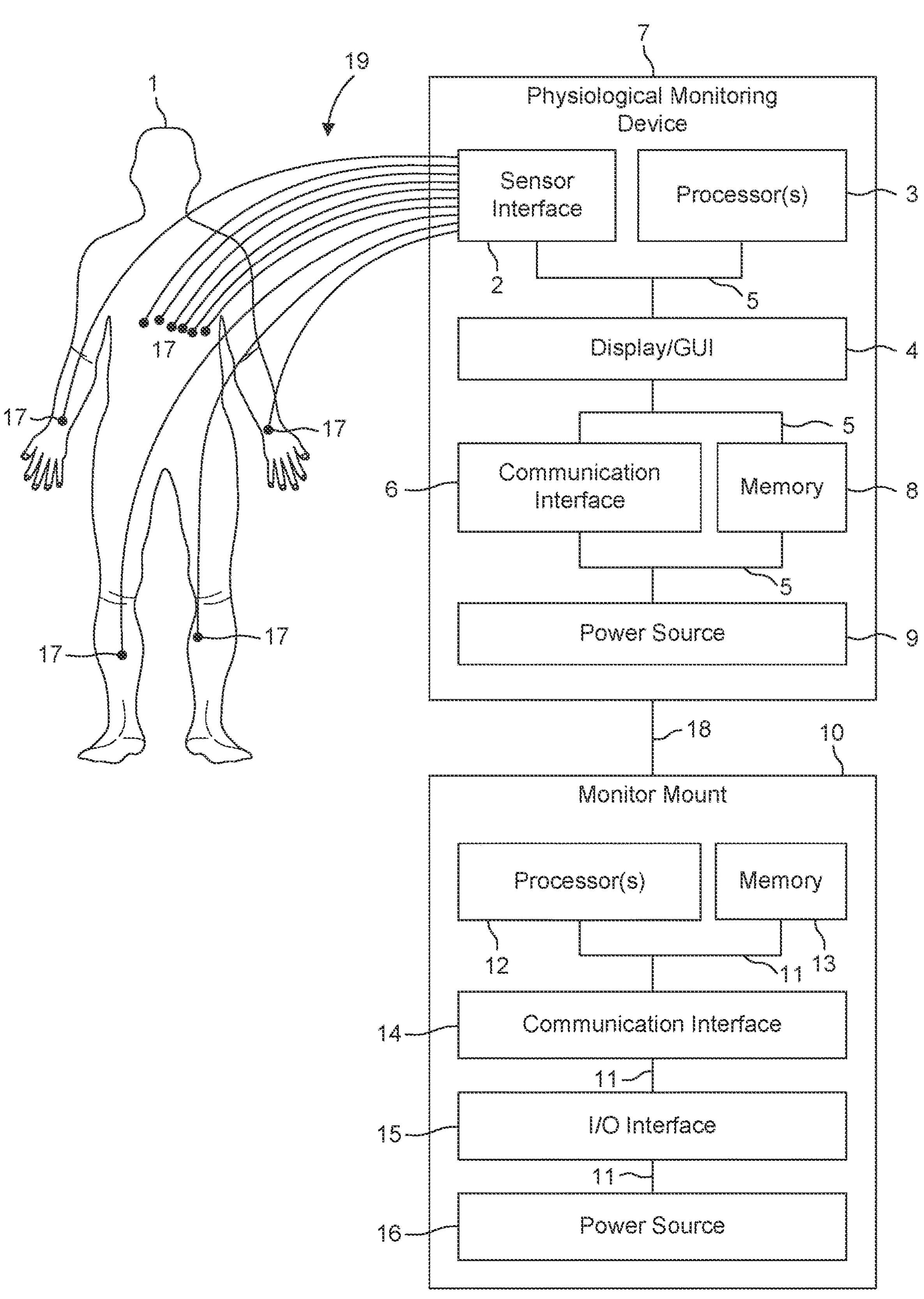
FIG. 1 shows a physiological monitoring system according to one or more embodiments.

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized, and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

As used herein, the term "standard video file format" is means a widely used video container format, such as MP4, AVI, MOV, or WMV.

Instructions may be executed by one or more processors, such as one or more central processing units (CPU), digital signal processors (DSPs), general purpose microprocessors, application specific integrated circuits (ASICs), field programmable logic arrays (FPGAs), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto.

Signal conditioning, as used herein, refers to manipulating an analog signal in such a way that the signal meets the requirements of a next stage for further processing. Signal conditioning may include converting from analog to digital (e.g., via an analog-to-digital converter), amplification, filtering, converting, biasing, range matching, isolation and any other processes required to make a sensor output suitable for processing after conditioning.

FIG. 1 shows a physiological monitoring system according to one or more embodiments. As shown in FIG. 1, the system includes a patient monitor 7 (i.e., a physiological monitoring device) capable of receiving physiological data from various sensors 17 connected to a patient 1 (i.e., a local patient). A patient monitor is a device that is configured to receive physiological data from another device and either display a patient's physiological data, monitor a patient's physiological data, or both. A patient monitor may be configured to be worn by a patient, may be a hand-held device, may be docked to or undocked from a larger unit such as a monitor mount, and, thus, may be transportable or non-transportable. For example, a monitor mount may be a larger patient monitor or a console that has a docking interface or docking receptacle to which the patient monitor can be removably docked.

A patient monitor may have memory and one or more processors that are cooperatively configured to receive sensor data from one or more sensors, process the sensor data in order to monitor one or more physiological parameters, including deriving one or more of the physiological parameters from the sensor data, and control a display to display the monitored physiological parameters by one or more graphical or textual representations. Additionally, or alternatively, memory and at least one processor may be located on a network (e.g., on an external server or computer) that provides additional processing power and capabilities that may not be present on the patient monitor. In this case, the patient monitor may transmit the sensor data on a network to an external processor, which in turn derives one or more of the physiological parameters from the sensor data, performs monitoring functions on the physiological parameters, and transmits monitored data and/or display data back to the patient monitor for display on a display of the patient monitor. The transmissions on the network may be through wireless communication channels, wired communication channels, or a combination thereof, but should be sufficiently fast to enable monitoring and display of data in real-time.

In general, it is contemplated by the present disclosure that the patient monitor 7 includes electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the patient monitor 7 may be adapted to execute any operating system, including Linux, UNIX, Windows Server, etc., as well as virtual machines adapted to virtualize execution of a particular operating system, including customized and proprietary operating systems. The patient monitor 7 may be further equipped with components to facilitate communication with other computing devices over one or more network connections, which may include connections to local and wide area networks, wireless and wired networks, public and private networks, and any other communication network enabling communication in the system.

As shown in FIG. 1, the patient monitor 7 is, for example, a patient monitor implemented to monitor various physiological parameters of the patient 1 via the sensors 17. The patient monitor 7 includes a sensor interface 2, one or more processors 3, a display/graphical user interface (GUI) 4, a communication interface 6, a memory 8, and a power source 9. The sensor interface 2 can be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, sensors 17 may include electrodes that are attached to the patient 1 for reading electrical signals generated by or passed through the patient 1. Sensors 17 may be configured to measure vital signs, measure electrical stimulation, measure brain electrical activity such as in the case of an electroencephalogram (EEG), measure blood characteristics using absorption of light, for example, blood oxygen saturation fraction from absorption of light at different wavelengths as it passes through a finger, measure a carbon dioxide ($CO_2$) level and/or other gas levels in an exhalation stream using infrared spectroscopy, measure oxygen saturation on the surface of the brain or other regions, measure cardiac output from invasive and noninvasive blood pressure, measure temperature, measure induced electrical potentials over the cortex of the brain, measure blood oxygen saturation from an optical sensor coupled by fiber to the tip of a catheter. The data signals from the sensors 17 include, for example, sensor data related to an electrocardiogram (ECG), non-invasive peripheral oxygen saturation (SpO2), non-invasive blood pressure (NIBP), body temperature, end tidal carbon dioxide (etCO2), apnea detection, and/or other physiological data, including those described herein.

The one or more processors 3 are used for controlling the general operations of the patient monitor 7, as well as processing sensor data received by the sensor interface 2. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the patient monitor 7.

The processing of sensor data may include performing signal conditioning on the sensor data, monitoring the sensor data, deriving physiological parameters from the sensor data, monitoring the physiological parameters, comparing the sensor data and/or the physiological parameters to one or more thresholds, generating alarms based on the monitoring/comparison results, generating visual representations of the sensor data, the physiological parameters, and/or alarms, and displaying the visual representations, but is not limited thereto.

The display/GUI 4 is configured to display various patient data, sensor data, physiological parameters, and hospital or patient care information, and includes a user interface implemented for allowing interaction and communication between a user and the patient monitor 7. The display/GUI 4 includes, but is not limited to a liquid crystal display (LCD), cathode ray tube (CRT) display, thin film transistor (TFT) display, light-emitting diode (LED) display, high definition (HD) display, or other similar display device that may or may not include touch screen capabilities. The display/GUI 4 also provides a means for inputting instructions or information directly to the patient monitor 7. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators). The patient monitor 7 may also be connectable to additional user input devices, such as a keyboard or a mouse.

The communication interface 6 enables the patient monitor 7 to directly or indirectly communicate with one or more computing networks and devices, including one or more sensors 17, workstations, consoles, computers, monitoring equipment, alert systems, and/or mobile devices (e.g., a mobile phone, tablet, or other hand-held display device). The communication interface 6 can include various network cards, interfaces, communication channels, cloud, antennas, and/or circuitry to enable wired and wireless communications with such computing networks and devices. The communication interface 6 can be used to implement, for example, a Bluetooth connection, a cellular network connection, and/or a Wi-Fi connection with such computing networks and devices. Example wireless communication connections implemented using the communication interface 6 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol).

Additionally, the communication interface 6 can enable direct (e.g., device-to-device or point-to-point) communications (e.g., messaging, signal exchange, etc.) to the patient monitor 7 using, for example, a universal serial bus (USB) connection or another communication protocol interface, such as service-oriented device connectivity (SDC). The communication interface 6 can enable direct device-to-device connection to other device such as to a tablet, a computer, a data distribution device, or similar electronic device; or to an external storage device or memory. A point-to-point connection according to the SDC protocol may be used for providing a remote view cluster service that enables the display 4 to display a local view pertaining to the local patient and a remote view of one or more remote patients. Accordingly, communication interface 6 can include an SDC interface that is connected to an SDC connection or communication channel that interfaces with another device, such as a remote view distribution device (RVDD).

The memory 8 can be a single memory device or one or more memory devices at one or more memory locations that include, but is not limited to, a random access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 can be used to store any type of instructions and patient data associated with algorithms, processes, or operations for controlling the general functions and operations of the patient monitor 7.

The power source 9 can include a self-contained power source such as a battery pack and/or include an interface to be powered either directly or indirectly through an electrical outlet. The power source 9 can also be a rechargeable battery that can be detached allowing for replacement. In the case of a rechargeable battery, a small built-in back-up battery (or super capacitor) can be provided for continuous power to be provided to the patient monitor 7 during battery replacement. Communication between the components of the patient monitor 7 (e.g., components 2, 3, 4, 6, 8, and 9) are established using an internal bus 5.

Accordingly, the patient monitor 7 is attached to one or more of several different types of sensors 17 configured to measure and readout physiological data related to the patient 1 (e.g., as shown on the left side of FIG. 1). One or more sensors 17 may be attached to patient monitor 7 by, for example, a wired connection coupled to the sensor interface 2. Additionally, or alternatively, one or more sensors 17 may be a wireless sensor that is communicatively coupled to the patient monitor 7 via the communication interface 6, which includes circuitry for receiving data from and sending data to one or more devices using, for example, a Wi-Fi connection, a cellular network connection, and/or a Bluetooth connection.

As shown in FIG. 1, the patient monitor 7 may be connected to a monitor mount 10 via a connection 18 that establishes a communication connection between, for example, the respective communication interfaces 6, 14 of the devices 7, 10. The connection 18 is an interface that enables the monitor mount 10 to detachably secure the patient monitor 7 to the monitor mount 10. In this regard, "detachably secure" means that the monitor mount 10 can receive and secure the patient monitor 7, but the patient monitor 7 can also be removed or undocked from the monitor mount 10 by a user when desired. In other words, the patient monitor 7 can be removably docked or removably mounted to the monitor mount 10 and the connection 18 forms an electrical connection between the devices 7, 10 for enabling communication therebetween.

The connection 18 may enable the patient monitor 7 to transmit sensor data acquired from sensors 17 to the monitor mount 10 to be processed and analyzed by processor(s) 12 integrated within the monitor mount 10. The connection 18 may enable the monitor mount 10 to transmit processed sensor data, measured physiological parameters derived from the sensor data, and/or control signals to the patient monitor 7. Control signals may include instructions for controlling the display of data, images, graphics, text, indicators, and/or icons on the display 4 of the patient monitor 7. These control signals may be received by a processor 3 of the patient monitor 7, which in turn controls the imagery on the display 4 accordingly. The monitor mount 10 may also be connected to a network (e.g., a hospital network) and cooperatively exchanges information therewith for the processing of data and the generation of control signals.

The connection 18 may also enable the transmission of power from the monitor mount 10 to the patient monitor 7 for charging the power source 9. The connection 18 may also enable the patient monitor 7 to detect whether it is in a docked or undocked state. Thus, the connection 18 may further enable the patient monitor 7 via the interface to detect an undocking event and a docking event by detecting an electrical connection or an optical link, or an absence thereof, between the patient monitor 7 and the monitor mount 10.

The connection 18 may include, but is not limited to, a USB connection, a parallel connection, a serial connection, a coaxial connection, a High-Definition Multimedia Interface (HDMI) connection, an optical connection, and/or any other electrical connection configured to connect electronic devices and transmit data and/or power therebetween.

The monitor mount 10 includes one or more processors 12, a memory 13, a communication interface 14, an I/O interface 15, and a power source 16. The one or more processors 12 are used for controlling the general operations of the monitor mount 10 and may be further used to controller one or more operations of the patient monitor 7 when mounted to the monitor mount 10. Each one of the one or more processors 12 can be, but are not limited to, a CPU, a hardware microprocessor, a multi-core processor, a single core processor, an FPGA, a microcontroller, an ASIC, a DSP, or other similar processing device capable of executing any type of instructions, algorithms, or software for controlling the operation and performing the functions of the monitor mount 10.

The memory 13 can be a single memory or one or more memories or memory locations that include, but are not limited to a RAM, a memory buffer, a hard drive, a database, an EPROM, an EEPROM, a ROM, a flash memory, hard disk, or various layers of memory hierarchy, or any other non-transitory computer readable medium. The memory 13 can be used to store any type of instructions associated with algorithms, processes, or operations for controlling the general functions and operations of the monitor mount 10.

The communication interface 14 allows the monitor mount 10 to communicate with one or more computing networks and devices (e.g., the patient monitor 7, workstations, consoles, computers, monitoring equipment, alert systems, and/or mobile devices (e.g., a mobile phone, tablet, or other hand-held display device). The communication interface 14 can include various network cards, interfaces, communication channels, antennas, and/or circuitry to enable wired and wireless communications with such computing networks and devices. The communication interface 14 can also be used to implement, for example, a Bluetooth connection, a cellular network connection, cloud-based connection, and a Wi-Fi connection. Example wireless communication connections implemented using the communication interface 14 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

The communication interface 14 can also enable direct (i.e., device-to-device) communications (e.g., messaging, signal exchange, etc.) such as from the monitor mount 10 to the patient monitor 7 using, for example, the connection 18.

The communication interface 14 can enable direct device-to-device connection to another device such as to a tablet, a computer, a data distribution device, or similar electronic device; or to an external storage device or memory. A point-to-point connection according to the SDC protocol may be used for providing a remote view cluster service that enables the patient monitor 7 while docked to the monitor mount 10 to display a local view pertaining to the local patient and a remote view of one or more remote patients. Accordingly, communication interface 14 can include an SDC interface that is connected to an SDC connection or communication channel that interfaces with another device, such as a remote view distribution device The I/O interface 15 can be an interface for enabling the transfer of information between monitor mount 10, one or more physiological monitoring devices 7, and external devices such as peripherals connected to the monitor mount 10 that need special communication links for interfacing with the one or more processors 12. The I/O interface 15 can be implemented to accommodate various connections to the monitor mount 10 that include, but is not limited to, a USB connection, a parallel connection, a serial connection, a coaxial connection, an HDMI connection, or any other electrical connection configured to connect electronic devices and transmit data therebetween.

The power source 16 can include a self-contained power source such as a battery pack and/or include an interface to be powered through an electrical outlet (either directly or by way of the patient monitor 7). The power source 16 can also be a rechargeable battery that can be detached allowing for replacement. Communication between the components of the monitor mount 10 (e.g., components 12, 13, 14, 15 and 16) are established using an internal bus 11.

Embodiments described herein are directed to remote view distribution for Actionable Bed-to-Bed Alarm that is provided by a remote view distribution device that is connected to a plurality of patient monitors or monitor mounts via SDC connections. Each SDC connection is a point-to-point connection from, for example, a patient monitor to the remote view distribution device. Other types of point-to-point connections are also possible. Thus, in general, embodiments are directed to a point-to-point network for patient data and remote view distribution. A point-to-point connection, sometimes called a point-to-point (P2P) link or a private line, securely connects two locations (e.g., end-points or nodes) using a Layer 2 data connection, thereby building a closed network data transport connection. Thus, there is only one transmitting device and one receiving device for each point-to-point connection, although the connection can be bidirectional between its nodes.

For Actionable Bed to Bed Alarm the loading on the patient monitors is complicated. The Actionable Bed-to-Bed Alarm supports the idea of Bed to Group alarms through the use of care groups. A care group is defined as a group of beds (i.e., a group of patient monitors) that are monitored by a group of care givers. In some critical wards, a care group will have one clinician per bed (i.e., per patient/patient monitor) in the group. In other less critical wards, there may be one clinician for every four beds (i.e., for every four patients/patient monitors). There may also be a mixture of critical and non-critical beds in the same care group. Because of the varied coverage of clinicians to the number of beds, the Actionable Bed-to-Bed Alarm can be configured to alarm and display a particular set of patients within the care group on a signal patient monitor. This includes displaying physiological data and alarms corresponding to a local patient that is directly assigned to the patient monitor and physiological data and alarms corresponding to one or more remote patients located remote to the patient monitor.

This configuration can be defined for each clinician. If several clinicians register their remote view of a critical patient, it is easy to see that the number of remote view connections can easily increase. As an example, a sixty-four bed care group could have sixteen clinicians that could all register on the same critical patient requiring at least sixteen connections from the critical bed (i.e., the patient monitor of the critical patient). That is, the patient monitor of the critical patient would require sixteen SDC connections in order to transmit phycological data and alarms to sixteen clinicians located at other remote display devices. Such a configuration would be complex, cumbersome, and expensive. Ultimately, designing a patient monitor with sixteen SDC connections may not be practical due to the processing load.

In addition to loading issues for the Actionable Bed-to-Bed Alarm, there is also a latency requirement. The goal for the Actionable Bed-to-Bed Alarm is to show the information from the alarming bed (i.e., the remote patient monitor that generated an alarm) as soon as possible. In the case that the alarm is life threatening, every second of delay in the alarm structure is a second lost in treating the patient. An objective of the described remote view distribution system is to provide a latency from a remote patient monitor to a display of a local patient monitor of no more than two seconds, and, more preferably, no more than 1 second.

Accordingly, a remote view distribution device is introduced that is connected to each patient monitor via a physical SDC connection for point-to-point bi-directional communication. The SDC connection can be represented by two virtual connections, each of which enables communication to flow in one direction. The remote view distribution device is a network device that has two virtual connections to each device on the network (e.g., to each patient monitor). The first connection is to receive all of the patient data of a respective patient through an SDC connection. The patient data can include demographics data of the patient (e.g., age, height, weight), sensor data from one or more sensors, physiological data, video data, and/or alarm data that is either passed through, processed by, or generated by the patient monitor or another data source. The second connection is a new type of connection that will provide a fast means to transmit remote view data back to a patient monitor or display device. This second connection may contain remote view data from multiple patients (i.e., from multiple patient monitors or multiple data sources).

The input and output connections to the patient monitor 7 or the monitor mount 10 are virtual connections since there is only one physical connection from a patient monitor. In other words, each patient monitor or display device has a single physical SDC connection to the remote view distribution device that provides the two virtual connections for bi-directional data transmission. A "physical" connection can be a wired or wireless connection. In addition to this remote view distribution device, a remote view cluster service is defined as a mechanism for patient monitors to receive remote view data from other patient monitors connected to the remote view distribution device.

Figure 2A:
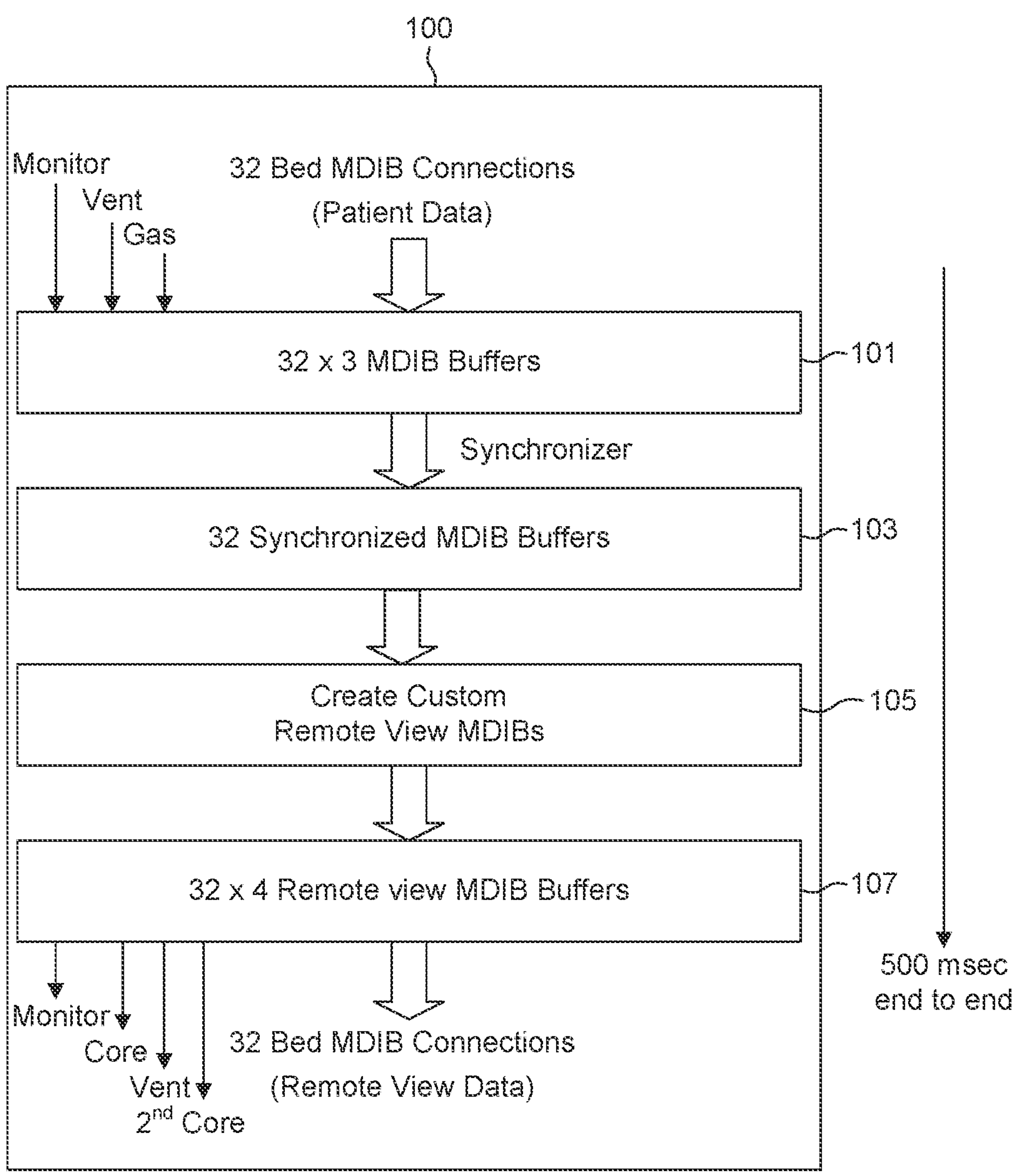
FIG. 2A illustrates a block diagram of a remote view distribution device according to one or more embodiments.

FIG. 2A illustrates a block diagram of a remote view distribution device 100 according to one or more embodiments. In this example, the remote view distribution device 100 is connected via 32 SDC connections to 32 beds or patient monitors with a point-to-point SDC connection being established with the remote view distribution device 100 for each bed. As noted above, each bed corresponds to a different patient and may refer to a patient monitor 7 or a monitor mount 10 as a patient data source. Additionally, other patient data sources can also be connected to the remote view distribution device 100, either directly via an SDC connection or indirectly through a patient monitor 7 or a monitor mount 10. These other patient data sources include a ventilator, a therapy device, a respiratory assistance gas tank, or a camera. These data sources could be connected to a patient monitor 7 or monitor mount 10 that then forwards the respective patient data to the remote view distribution device 100 via an SDC connection.

The remote view distribution device 100 includes medical data information base (MDIB) input buffers 101 that receive patient data (e.g., MDIBs) from the 32 SDC connections and stores the received patient data for further processing and/or forwarding. In particular, the remote view distribution device 100 extracts the pertinent data from the received MDIBs to construct the input buffers. An MDIB is a type of data block that is a collection of data objects that are provided by a particular medical device including descriptive and state information. An MDIB may be constructed by a patient monitor 7 based on a collection of data objects (e.g., waveforms, physiological parameters, descriptive information, and state information) from one or more sensors and transmitted to the remote view distribution device 100 as the patient data.

The remote view distribution device 100 includes a synchronizer 103. In particular, the patient monitors 7 transmit patient data to the remote view distribution device 100 asynchronously as respective patient data changes in real-time. The synchronizer 103 is configured to synchronize the patient data received from different beds (e.g., based on a synchronization signal) so that the data is not changing while being accessed by the remote view distribution device 100 for generating remote views. Thus, a synchronization layer is added to the data pipeline so that the processor 105 of the remote view distribution device 100 has a stable buffer to work with.

The remote view distribution device 100 includes a remote view processor 105 that receives the synchronized MDIBs from the synchronizer 103 and generates remote view MDIBs therefrom to create custom remote views for each of the patient monitors 7. To create a remote view MDIB for a particular patient monitor 7, the processor 105 may first select MDIBs that correspond to remote patients that are assigned to that patient monitor 7. For example, the patient monitor 7 may be connected to a local patient for a local view and assigned to three other remote patients for a remote view on its display 4. The processor 105 is configured to select the MDIBs pertaining to the three remote patients for creating a remote view that will be displayed on the patient monitor 7. Once the pertinent MDIBs are selected, the processor may further select certain data objects from each of the MDIBs for the remote view. In other words, not all data objects for remote view may be relevant for a remote view depending on a remote view setting configured by a user and the state of the alarms. Thus, data objects that are selected may change based on user setting. Once the pertinent data objects are extracted from the selected sub-set of MDIBs by the processor 105, the processor 105 uses the extracted data objects to generate a remote view MDIB, which is a collection of the extracted data objects that are arranged for remote viewing. In this case, 32 custom remote view MDIBs are generated, with each remote view MDIB being assigned to a different one of the patient monitors 7.

The remote view distribution device 100 includes remote view data buffers 107 that receive the custom remote view MDIBs for transmission to the respective patient monitors 7 via a respective SDC connection and transmits the remote view MDIBs to their assigned patient monitors 7 (e.g., based on remote view configuration information). Remote view configuration information may control which data objects are extracted from a particular MDIB for inclusion in a remote view MDIB as well as control which patient monitor or monitors receive a particular remote view MDIB. Thus, the remote view configuration information indicates how each remote view MDIB is constructed from data objects extracted from one or more MDIBs and identifies which patient monitors are to receive each remote view MDIB.

A patient monitor 7 that receives a remote view MDIB is configured to generate a remote view on its display 4 according to the remote view data (i.e., remote patient data of one or more remote patients) contained within the remote view MDIB. Thus, a single SDC connection can transmit remote view data from multiple patients to a patient monitor 7 for displaying.

The remote view distribution device 100 is a scalable design. It is envisioned that the remote view distribution device 100 would have several card slots and that additional input/output channels can be added by inserting additional cards. The smallest scale would be a device that can handle at least 4 inbound patients. The largest system will be set by the processing power of the remote view distribution device 100 as well as the aggregate bandwidth needed on the local area network (LAN) connection port. The maximum number of inbound connections is estimated to be between 32 and 128 devices, but is not limited thereto.

Additionally, beds (e.g., patient monitors 7) may be grouped into alarm groups and the remote view distribution device 100 is configured to generate remote views for each alarm group (i.e., on a group-by-group basis). In this way, the remote view distribution device 100 may include one output for each alarm group, as opposed to one for each bed.

The remote view distribution device 100 may be configured to operate in conjunction with an Alarm Group Service (AGS) module 120. The AGS module 120 is a processing module that generates alarm group configuration information that describes which beds belong to which alarm group. In other words, the AGS module 120 indicates how the different patient monitors 7 are arranged into different groups. The AGS module 120 can also inform the beds which beds are in alarm via group alarm data. SDC does not allow tight coupling between devices. Therefore, the AGS module 120 does not forward messages to the remote view distribution device 100. Instead, all of the transaction between the bed and the AGS module 120 are done through the MDIB. In other words, the AGS module 120 provides the alarm group configuration information and alarm states to the patient monitor 7, and the patient monitor 7 generates its MDIBs to include this information. In order for the remote view distribution device 100 to receive the latest alarm group configuration as well as which beds are in alarm, the remote view distribution device 100 simply needs to listen (parse) to the bed's MDIB.

The MDIBs of each bed (i.e., of each patient monitor) contain the alarm group configuration for that bed so when the MDIB is read by the remote view distribution device 100, it determines which alarm group a particular bed is in. Additionally, an MDIB may include bed alarm data that is specific to the patient monitor 7 that generates the MDIB and is specific to a particular patient/bed. In other words, patent monitor 7 generates an MDIB that include bed alarm data that is specific to its local patient.

The AGS module 120 may be separate from the remote view distribution device 100, may be integrated with the remote view distribution device 100, or both. An AGS can be run on its own. It could run on a device on the network (e.g., 120-1 and 120-2). However, it only outputs a single text message per bed. This is the entry level remote view service. The remote view distribution device 100 includes a copy of the AGS module 120. It needs to have a copy of the AGS module 120 for latency reasons. The AGS module 120 is designed in a way that it can be replicated and run in parallel with other instances of the AGS.

Additionally, or alternatively, alarm groups may be modified or otherwise configured directly at the patient monitors 7 or at a central station 207, for example, by user input at the device. Thus, each patent monitor 7 is configured to generate alarm group configuration information based on one or more methods of receiving this information and inserting the alarm group configuration information into its MDIBs that are transmitted to the remote view distribution device 100. In this way, the MDIBs are updated to include this information that can be read by the remote view distribution device 100. The AGS module 120 may aggregate all alarm group information received from the network, including alarm groups selected at the central station or the patient monitors, into the alarm group configuration information.

The AGS module 120 may provide the logic of which bed requires alarm notification from other beds. When the AGS module 120 sends a bed a message about an alarm at another bed, it must also send that same message to the remote view distribution device 100 so that the remote view distribution device 100 can make the display information for the logical AGS module connections available for remote view. Alternatively, the remote view distribution device 100 may receive alarms directly from the patient monitor 7, thereby bypassing the AGS module 120, and insert the alarms into a respective remote view MDIB as display information. Alternatively, the AGS module 120 provides the alarm group configuration information and alarm states to the patient monitor 7, and the patient monitor 7 generates its MDIBs to include this information. The remote view distribution device 100 then receives this information in the MDIBs received from the patient monitor 7.

As noted above, the patient data packets (inbound data packets received by the remote view distribution device 100) are unsynchronized SDC packets that describe the changes to an MDIB. Thus, when new patient data packets are received, respective MDIBs can be updated by the MDIB buffer 101. Other data structures for creating remote view data blocks are contemplated. A balance between using the MDIB structure to pass display information compared with creating a different data structure that is optimized for generating a remote view picture at the patient monitor 7 should be considered. A general requirement for the Actionable Bed-to-Bed Alarm function is to have 1-16 patients connected to the remote view on a single bedside monitor. Table 1 provides possible Actionable Bed-to-Bed Alarm configurations.

TABLE 1

| # of Patients | # of Viewable Waveforms Per Patient | # of Viewable Parameters Per Patient | Actionable Bed to Bed Alarm Configuration |
|---|---|---|---|
| 1 | 8 | 32 | 1 × 8 |
| 2 | 8 | 32 | 2 × 8 |
| 4 | 4 | 16 | Cluster 4 × 4 |
| 8 | 1 | 4 | Central 8 |
| 16 | 1 | 4 | Central 16 |

As more patients are added to the remote view of another bed, the number of viewable waveforms per patient is decreased. The 8 and 16 Bed Central view can only display a single waveform channel for each remote patient.

The delay time from the onset of an alarm to the time a corresponding waveform is rendered on the display 4 of the remote view monitor is critical for the Actionable Bed to Bed Alarm function. The initial timing budget is shown in Table 2.

TABLE 2

| Function | Target Duration |
|---|---|
| Alarm recognition from Core of Patient Monitor | Start |
| Patient monitor alarms and sends message to remote view distribution device | 100 msec |
| Remote view distribution device receives patient data and synchronizes to other beds | 100 msec |
| Remote view distribution device receives alarm data and reconfigures outbound data | 500 msec |
| Bed receives remote view distribution device outbound data and generates waveforms on display | 500 msec |
| Total Delay | 1.2 seconds |

The remote view distribution device 100 requires time to assemble outbound packets from a mixture of input MDIB structures. The remote view distribution device 100 refers to a logic connection list (e.g., a device mapping) and makes the same connections from the input MDIBs to the outbound data packets. The remote view distribution device 100 follows a fixed set of rules to extract the waveform data from an input MDIB. For example, the first waveform is usually a primary ECG lead. For the central views, this may be the only waveform from an input MDIB that would be inserted into the outbound data packet (i.e., into a custom remote view MDIB). For remote views that have 4 or 8 waveforms per patient, there may be a fixed priority order regarding which available waveforms are to be extracted from an input MDIB for a custom remote view MDIB. For example, two primary ECG lead waveforms, an SPO2 waveform, and arterial invasive blood pressure (IBP) waveform may be extracted in that order for insertion into a custom remote view MDIB. Other waveforms in the input MDIB are disregarded by the processor 105 for generating the custom remote view MDIB.

The size of the input SDC packets is much larger than the output SDC packets. The processor 105 in the remote view distribution device 100 selects the appropriate data out of the inbound MDIB and copies it to the output packets (i.e., into the custom remote view MDIB). This selection process can be thought of as a data filter and reduces the data from the inbound data to only the data needed to create the remote view. The input to the processor 105 used to determine which data is selected for the outbound data may be received from the AGS module or may be preconfigured via mode selection or preprogrammed by some other logic rule set.

In the case where the AGS module has not set an output for a particular remote view, for example, since there are no active alarms in that care group, a patient monitor 7 may configure its own remote view by sending the appropriate request to the remote view distribution device 100. For example, a user may select which remote view is desired at the patient monitor 7 itself and the patient monitor 7 may transmit configuration information to the remote view distribution device 100 for configuring the remote view to be received from the remote view distribution device 100 at that patient monitor. This may include which remote patients are of interest and which waveforms should be provided for those patients. Different waveforms may be individually selected for each patient or the selected waveforms may be uniform across all selected remote patients or preconfigured according to a priority rule set, as described above. Thus, the configuration information may be a request from a patient monitor that indicates the desired information for a custom remote view. The remote view distribution device 100 may compile the configuration information received from each patient monitor as remote view configuration information. Alternatively, an AGS module 120 or other device may compile this configuration information into the remote view configuration information and transmit the remote view configuration information to the remote view distribution device 100. Alternatively, the AGS module 120 provides remote view configuration information, including the alarm group configuration information and alarm states, to the patient monitor 7, and the patient monitor 7 generates its MDIBs to include this information. The remote view distribution device 100 then receives this information in the MDIBs received from the patient monitor. The remote view distribution device 100 can then parse out this information from the MDIBs for use in constructing the custom remote view MDIBs.

The remote view distribution device 100 is configured to use this configuration information for customizing the remote view MDIBs for each bed (e.g., for each patient monitor 7). In other words, each remote view MDIB is individually customized by the remote view distribution device 100 for each outgoing remote view and output via its respective SDC connection. Each outgoing remote view includes a unique set of remote patients and corresponding waveforms and/or physiological data. The display device then receives a respective remote view MDIB and generates a remote view with remote patient information or remote bed information, including the display of one or more waveforms and/or physiological parameters contained within the remote view MDIB. The remote view distribution device 100 may be configured to graphically render the unique set of remote patients and corresponding wave forms and/or physiological parameters contained within each outgoing remote view MDIB and transmit the graphically rendered remote view MDIB to the patient monitor 7 in a standard video file format, such as MP4 video format. The estimated amount time for the remote view distribution device 100 to output the 32 custom remote view MDIBs is 500 msec from the time patient data is initially received.

The delay time for the Actionable Bed-to-Bed Alarm function is a critical parameter for the remote view function. In order to minimize the delay, there are some assumptions that can be made when estimating the target durations above. First, the remote view distribution device 100 is always connected to a bed (i.e., a patient monitor 7) for both input and output transmissions, independent of the state of any alarms. This is done to eliminate the connection time required to establish a connection during an alarm. Second, all remote view data will be sent via a single connection back to the requesting device even though it may contain data on up to 16 different patients. This minimizes processing power at the receiving device (e.g., at the patient monitor 7). Third, data is preferably transmitted in a data format that minimizes the time required to generate waveforms and other physiological parameters on display 4.

When the number of beds in a care facility exceeds the remote view distribution device's capacity for a number of simultaneous connections, multiple remote view distribution devices 100 can be deployed. For this discussion, the capacity of a remote view distribution device 100 to the same size as the care group. Within each care group, there are no restrictions to the number of groupings of alarms or the number of beds that a single bed can be associated with from an alarm point of view. There can also be a guaranteed delivery time of alarms and alarm waveforms to remote views.

Figure 2B:
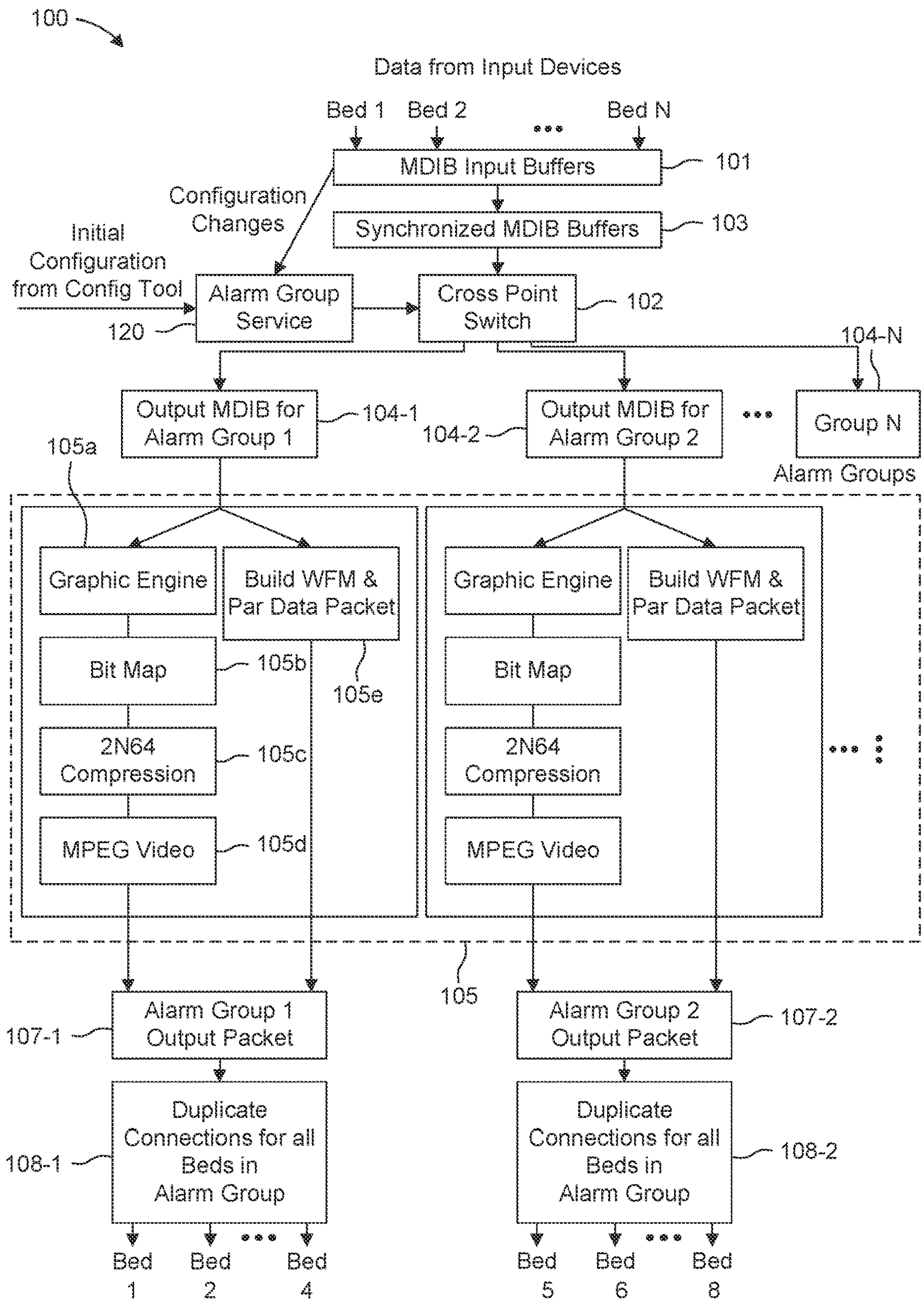
FIG. 2B illustrates a more detailed block diagram of a remote view distribution device according to one or more embodiments.

FIG. 2B illustrates a more detailed block diagram of a remote view distribution device 100 according to one or more embodiments. In this arrangement, the beds (patent monitors 7) are grouped into different alarm groups. The remote view distribution device 100 generates a single output packet (i.e., a single remote view MDIB) for each alarm group.

The alarm groups are configured in one of the manners described above. Initially, the AGS module 120 may configure the alarm groups based on an initial configuration received from a configuration tool. The AGS module 120 may provide the initial alarm group configuration that identifies which beds are in which groups to a cross-point switch 102. The cross-point switch 102 is configured to selectively route input MDIBs to different processing threads based on the alarm group configuration, where each processing thread is assigned to a different alarm group. Ultimately, N alarm groups may be configured. The cross-point switch 102 is further configured to extract or parse out alarm group configuration information from the input MDIBs and update the routing of the input MDIBs to their corresponding alarm groups based on the alarm group configuration information extracted from the input MDIBs.

An intermediary set of buffers 104-1, 104-2 . . . 104-N are configured to receive the input MDIBs that have been selectively routed by the cross-point switch 102 and provide them to a corresponding processing thread of processor 105. Each processing thread includes a graphic engine **105*a*, a bit map 105*b*, a 2N64 compression module 105*c*, an MPEG video generator 105*d*, and a waveform and parameter data generator 105*e***.

Remote view data buffers 107-1, 107-2 . . . are each configured to receive the outputs of a corresponding processing thread and construct a custom remote view MDIB by combining the MPEG video and the generated data packet that includes the waveform and parameter data. An output MDB distribution interface 108-1, 108-2, . . . then duplicates the connections for all beds (e.g., patient monitors 7) in its alarm group and transmits the custom remote view MDIB to the beds assigned to its alarm group.

Figure 3:
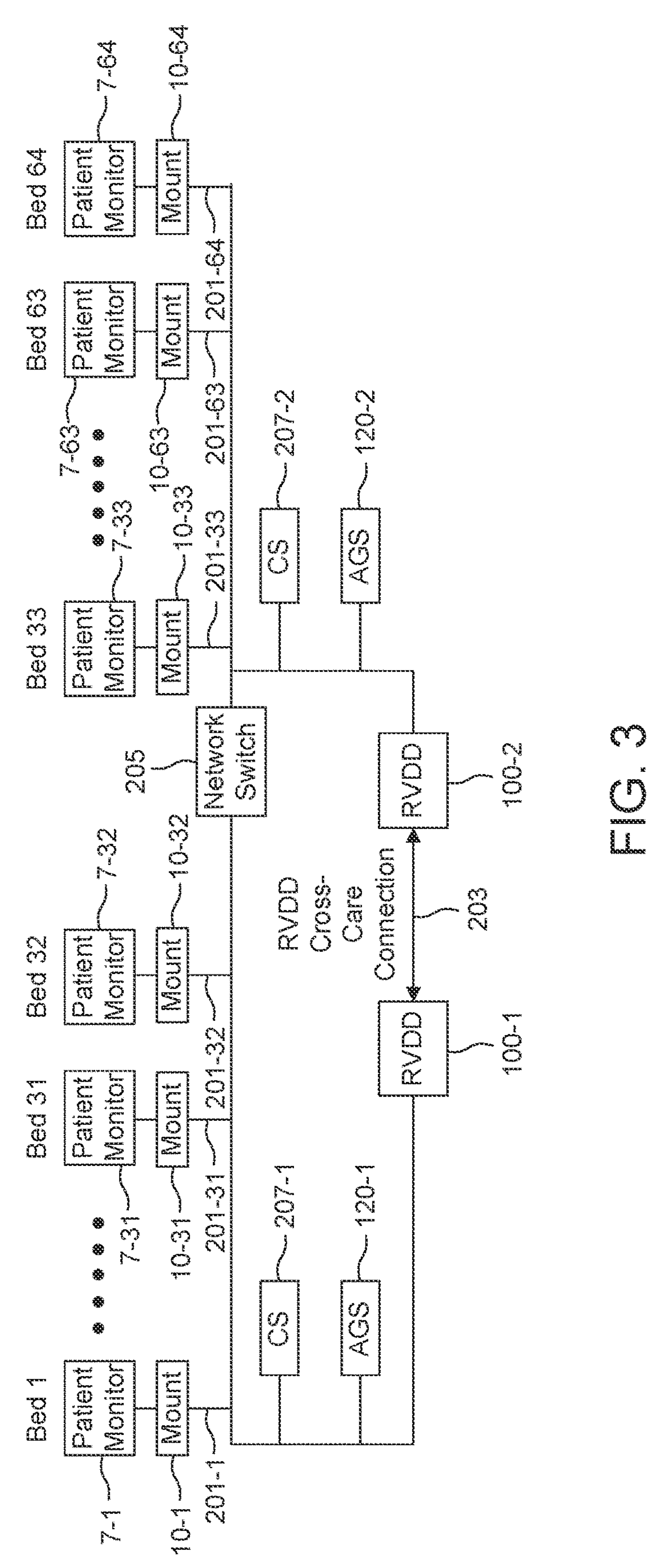
FIG. 3 illustrates a block diagram of a remote view distribution system according to one or more embodiments.

FIG. 3 illustrates a block diagram of a remote view distribution system 200 according to one or more embodiments. The remote view distribution system 200 includes 64 beds (Beds 1-64), each with a respective patient monitor 7 (patient monitors 7-1 to 7-64) that are connected to a remote view distribution network via a respective SDC connection 201-1 to 201-64. Each bed may also have a respective monitor mount 10 (monitor mounts 10-1 to 10-64) to which a respective patient monitor 7 can be docked.

The remote view distribution network includes multiple remote view distribution devices 100, including RVDD 100-1 and RVDD 100-2 that are coupled together by a cross-care connection 203. This high-speed connection between multiple RVDDs allows the RVDDs to exchange data at the synchronized and processed level. Any bandwidth and CPU power reserved for this interconnection function will reduce the maximum number of beds that can be handled by a single RVDD. For example, 10% of the bandwidth and CPU power may be reserved for RVDD interconnections. For example, if it is determined that the maximum size of an RVDD is 64 beds, then a bandwidth would be reserved for six interconnections between care units or RVDDs. These six connections could be of any of the view configurations types listed above.

The remote view distribution network can include sub-groups that are connected together by a network switch 205. Each sub-group includes a different set of beds, its own RVDD, and its own central station. The central stations 207-1 and 207-2 may be used to display a cluster view of all beds within its sub-group. In other words, they are configured as central monitoring stations that are configured to display remote views of all beds in its sub-group. Additionally, each RVDD 100-1 and 100-2 may be connected to a respective AGS module 120- and 120-2 that may be used to transmit remote view configuration information to its RVDD.

The connections to a remote view distribution device 100 are as follows: input MDIB data stream from N number of beds, where N is an integer greater than one; output remote view data buffer to each of N number of beds; an input from AGS module 120 to set the logic state of the remote view connections; an interconnection input/output to connect multiple RVDDs together, an input from beds to set logic state of remote view connections.

FIGS. 4A-4F illustrate an alarm propagation through a remote view distribution system according to one or more embodiments. The remote view distribution system includes a plurality of data sources that generate patient data monitor the patient data for an alarm (e.g., based on one or more thresholds), generates an alarm when one or more thresholds has been exceeded, and transmits the patient data and the alarm to a remote view distribution device 100 via a point-to-point connection, such as an SDC connection. In this case, the plurality of data sources are patient monitors 7-1 to 7-N, where N is 16 in this example. Thus, sixteen patient monitors are connected to the remote view distribution device 100 via a respective SDC connection.

Each SDC connection is represented by two virtual connections or pathways which are used to represent different transmission directions to and from the remote view distribution device 100. In other words, the two virtual connections between a patient monitor and the remote view distribution device 100 represent the bi-directional dataflow of a physical SDC connection. For example, the patient monitor 7-1 is connected to the remote view distribution device 100 by an SDC connection comprising an uplink connection 44-1 and a downlink connection 45-1. Similarly, patient monitor 7-N is connected to the remote view distribution device 100 by an SDC connection comprising an uplink connection 44-N and a downlink connection 45-N. The remote view distribution device 100 is configured to receive patient data and alarms (i.e., input packets or MDIBs) via the uplink connections 44-1 to 44-N and is configured to transit remote views (e.g., output packets or custom remote view MDIBs) via the downlink connections 45-1 to 45-N. The patient data can include one or more waveforms or other physiological parameter related to a patient.

Each patient monitor 7-1 to 7-N includes a display 4 with a local view 41 and one or more remote views 42 and 43. The local view 41 is an area of the display 4 allocated to displaying patient information of a local patient to which that patient monitor is locally monitoring. The patient information of the local patient is generated for display from measurements acquired by the patient monitor. The remote views 42 and 43 are areas of the display 4 allocated to displaying patient information of a respective remote patient to which that patient monitor is remotely monitoring. The patient information of the remote patient is measured by a remote patient monitor and is received by the patient monitor via the remote view distribution device 100.

In this example, twelve patient monitors are configured for remote monitoring of a patient in located bed 1 that corresponds to patient monitor 7-1. The alarm propagation illustrated in FIGS. 4A-4F will demonstrate how an alarm detected by patient monitor 7-1 is propagated to the remote views of those twelve "remote" patient monitors.

Figure 4A:
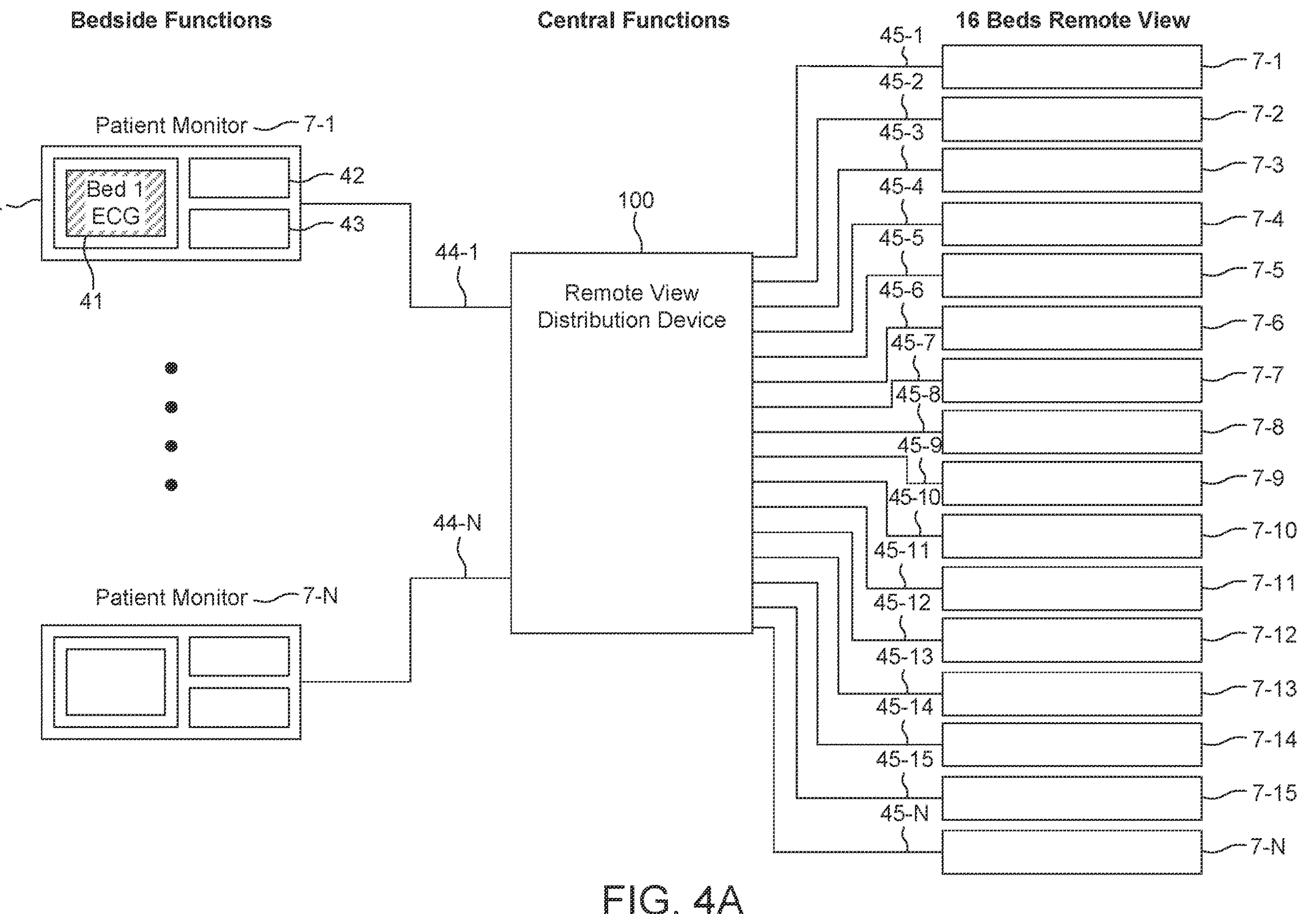
FIGS. 4A-4F illustrate an alarm propagation through a remote view distribution system according to one or more embodiments.

In FIG. 4A, patient monitor 7-1 generates an ECG waveform of its local patient and is monitoring the status of the ECG waveform. In this case, the patient monitor 7-1 determines that the ECG waveform is normal and no alarms are generated. Accordingly, the ECG waveform and other any other patient data is transmitted to the remote view distribution device 100 via its SDC connection 44-1, the remote view distribution device 100 generates twelve remote views (e.g., twelve remote view MDIBs, one for each patient monitor that is configured for remote monitoring of bed 1) that incorporate the ECG waveform, and the remote view distribution device 100 transmits the twelve remote views to their respective patient monitors via their respective SDC connections. At this time, the twelve remote views do not include any alarms related to bed 1.

Figure 4B:
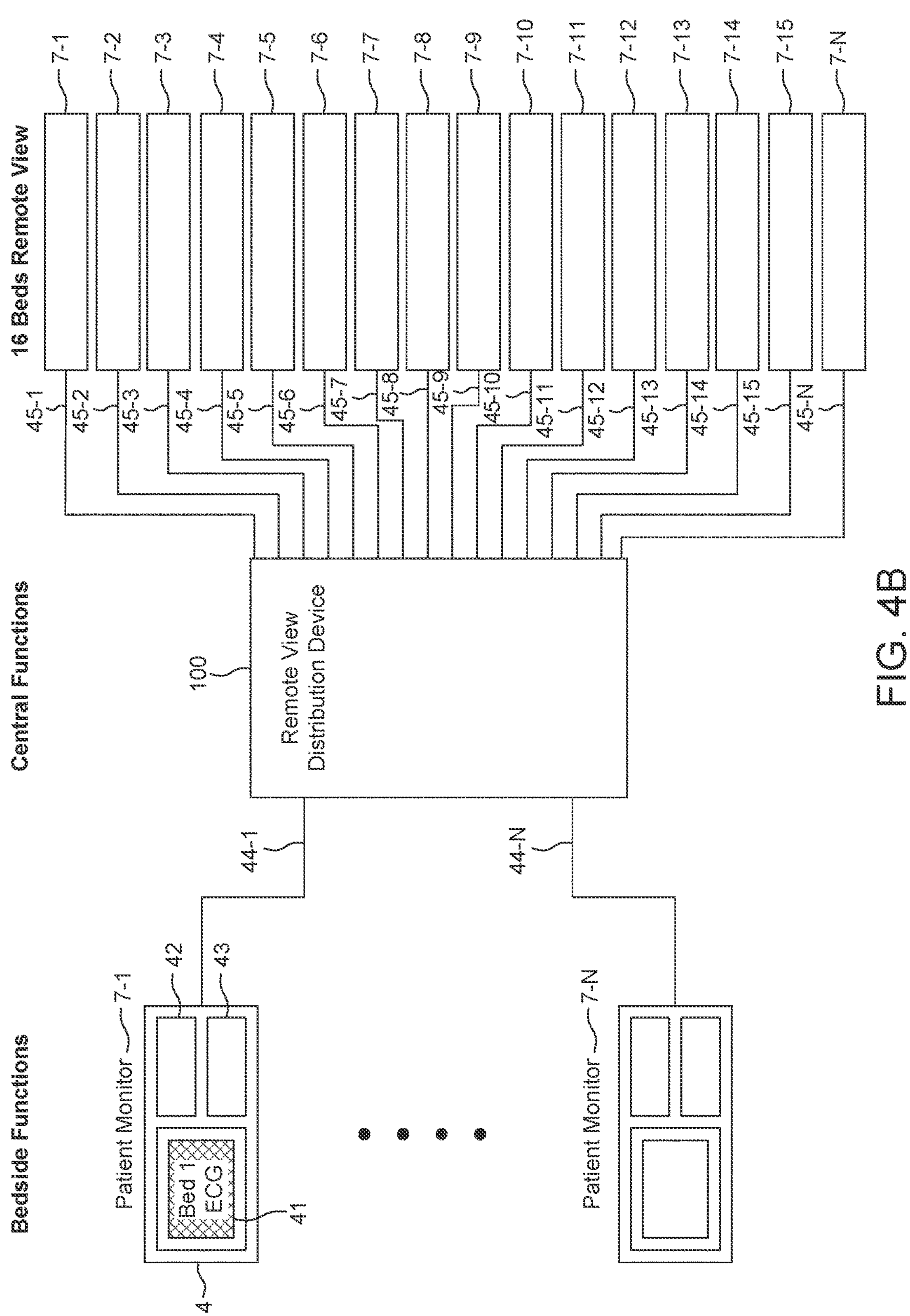

In FIG. 4B, patient monitor 7-1 detects an alarm due to an abnormal ECG waveform and generates the relevant alarm. The patient monitor 7-1 transmits the alarm along with the ECG waveform any other patient data to the remote view distribution device 100 via its SDC connection 44-1. The patient monitor 7-1 transmits the alarm and other patient data by updating its MDIB which is sent via its SDC connection 44-1 to the remote view distribution device 100.

Figure 4C:
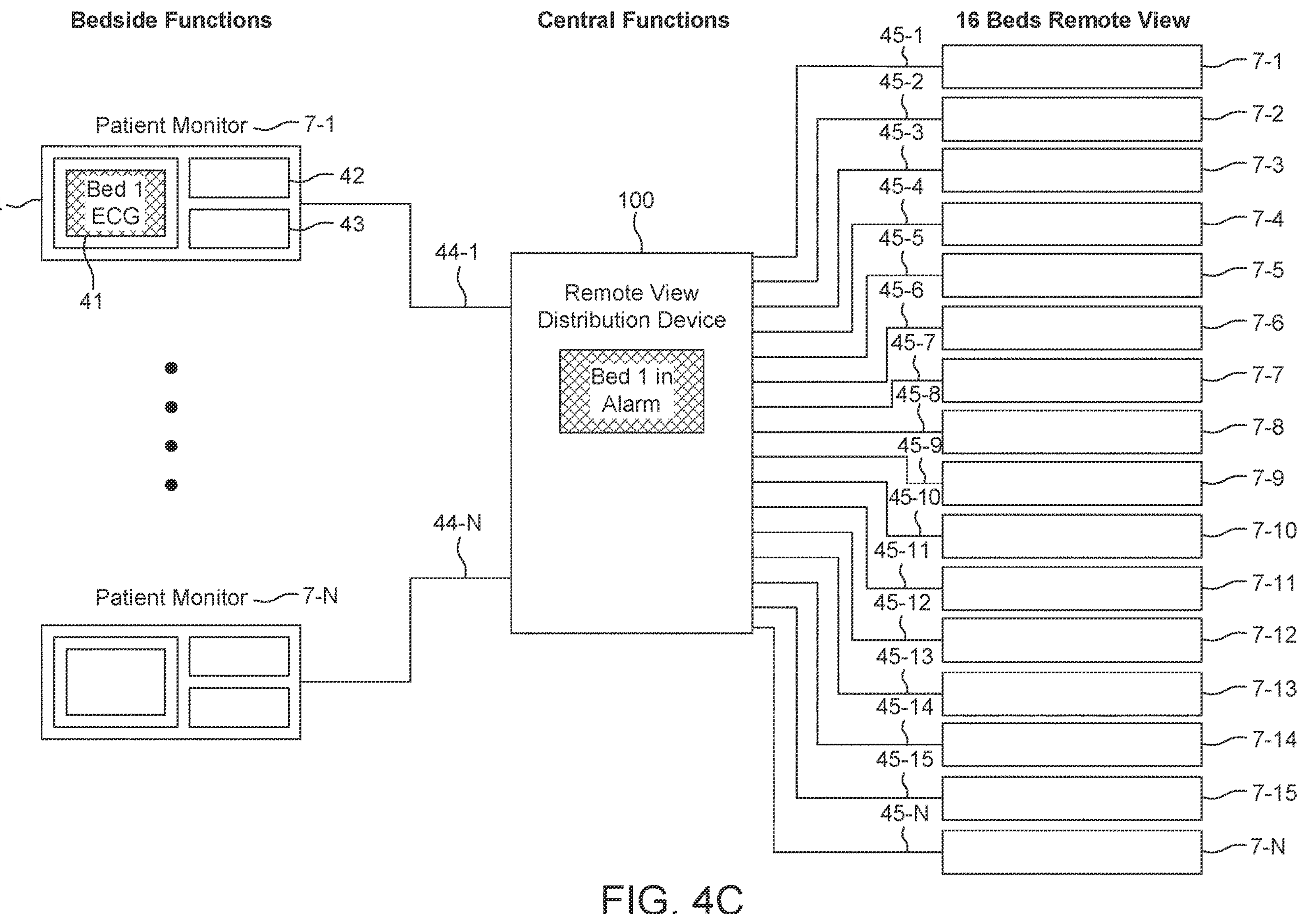

In FIG. 4C, the remote view distribution device 100 receives the patient data from the patient monitor 7-1, including the ECG waveform, the alarm, and any other patient data.

Figure 4D:
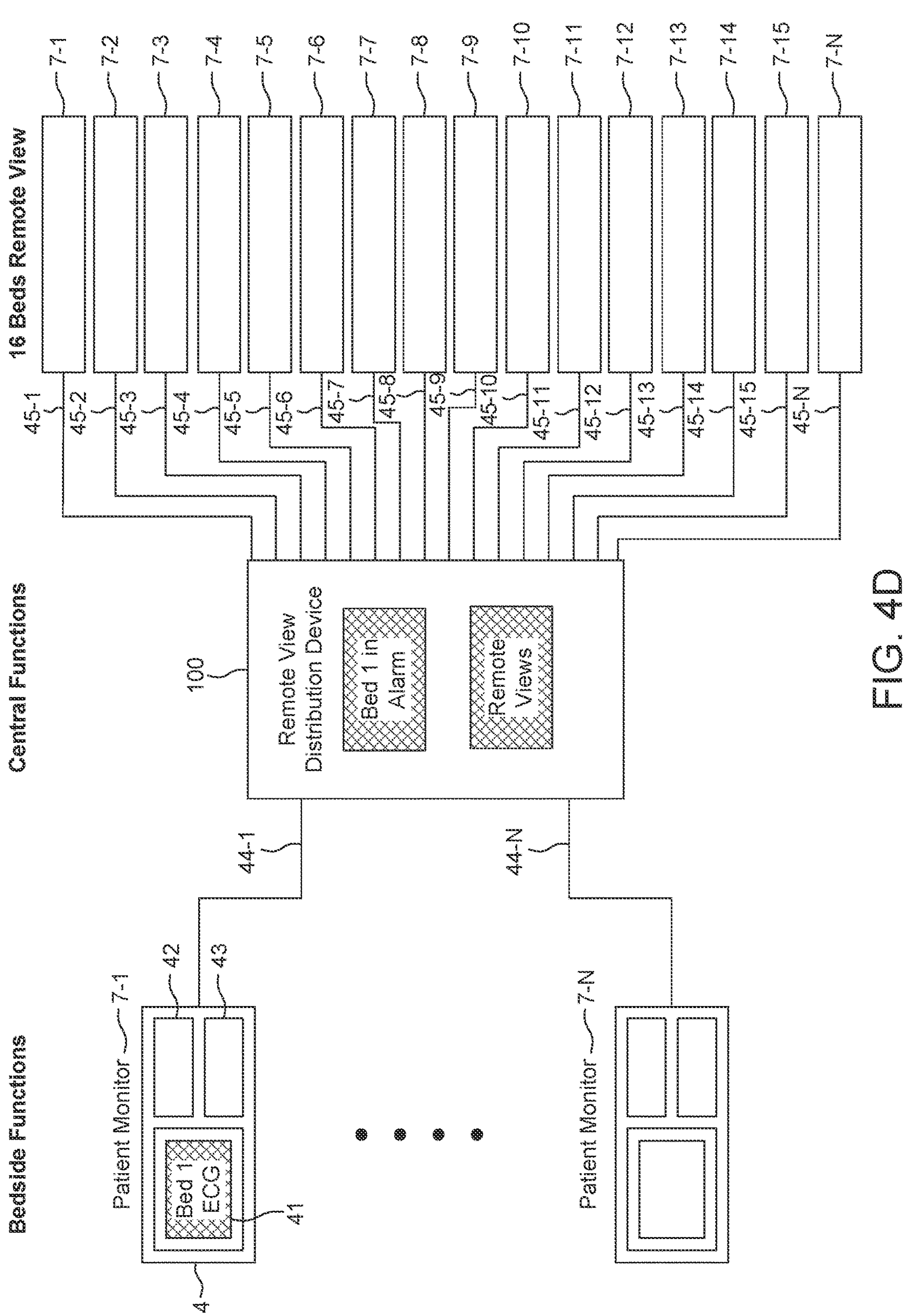

In FIG. 4D, the remote view distribution device 100 generates all remote views, and particularly, generates remote views corresponding to bed 1 that include the received alarm. For example, the remote view distribution device 100 generates remote views for any patient monitor that have bed 1 configured in its alarm group. In other words, the remote view distribution device 100 dynamically updates the twelve remote view MDIBs in real-time to include the alarm.

Figure 4E:
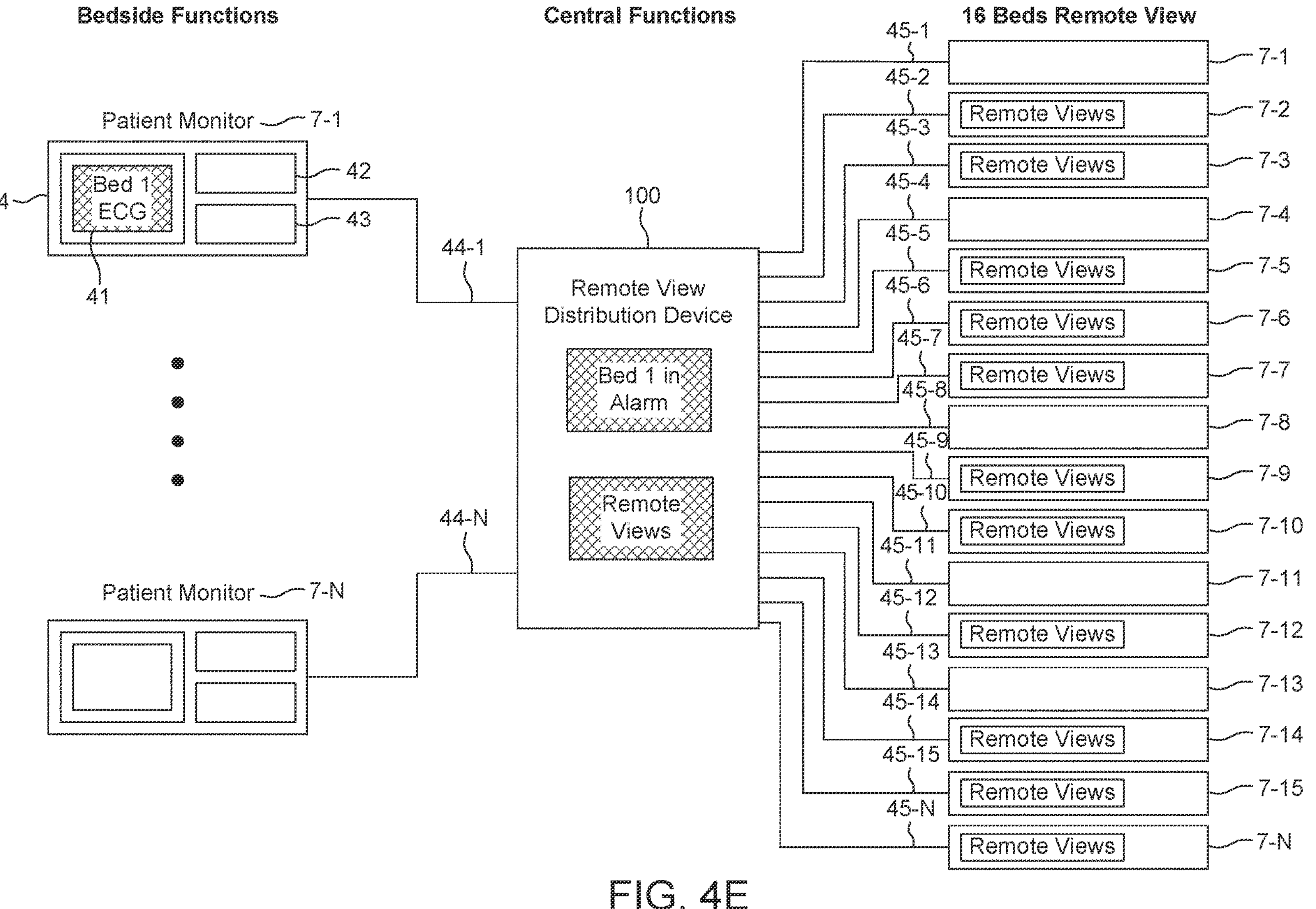

In FIG. 4E, the remote view distribution device 100 distributes the remote view MDIBs (i.e., the remote view data) to the relevant patient monitors that have bed 1 configured in their alarm group.

Figure 4F:
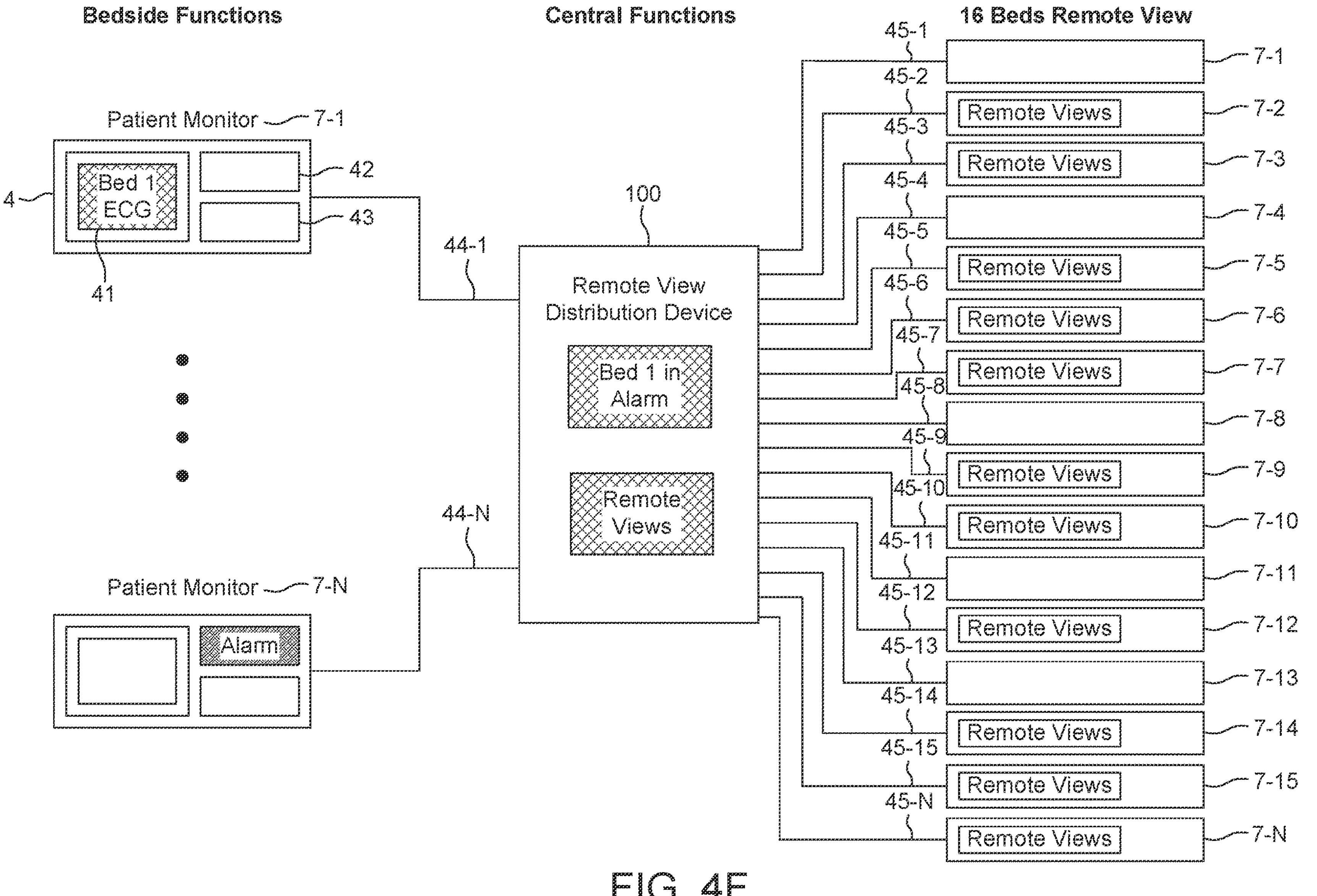

In FIG. 4F, the relevant patient monitors process the remote view MDIBs and render the remote views on their displays 4 with the alarm displayed for bed 1.

The back half of the RVDD architecture will now be described. The back half is defined as the processes after the data has been received by the remote view distribution device 100 and is ready to be used to construct output buffers. The first part of the process is to understand what the output buffers will look like when they are rendered on the receiving device. Next, the timing of what is rendered on the screen will be examined to see if having a few seconds of history is of value. Finally, the communication protocol will be analyzed for loading and response time.

There are two ways to construct the output buffers shown in the block diagrams. The first is the data model constructed by the waveform and parameter data generator 105*e*. Here, the data samples for the last five seconds for the waveforms are put into a time ordered buffer. The parameter value is copied into the output buffer since only the latest value is to be displayed. The second is a video model handled by the graphic engine 105*a*, the bit map 105*b*, the 2N64 compression module 105*c*, and the MPEG video generator 105*d*. If the output buffer is video, then a bit map is reserved in memory for an output buffer. Then, a graphics engine takes the waveform buffer as described above and renders the waveform on the screen. It will also render the parameter value. Once the video output buffer is constructed, it is compressed with a graphics engine and then sent out on the network.

There are many formats of the output buffers that are needed, however they can all be represented by two main formats. The two formats are 16 vertical channels or 8 vertical channels with two channels side-by-side on each vertical slot. FIG. 5A shows a first format of output buffers of the remote view distribution device 100 that comprises 16 vertical channels. FIG. 5B shows a second format of output buffers of the remote view distribution device 100 that comprises 8 vertical channels with two channels side-by-side. Each channel comprises of one waveform and a parameter box. Alternatively, each channel can contain four parameter boxes and no waveform. Each channel is sourced from one patient and multiple channels may be used for one patient.

One of the possible output formats for the communication channel between the remote view distribution device 100 and the devices that are rendering the remote views is compressed video. FIGS. 5C and 5D show additional formats of output buffers if compressed video is used. The video format would allow mixing of video and patient monitoring data.

FIGS. 6A-6F show different display formats of local and remote views rendered on a display according to one or more embodiments.

Figure 6A:
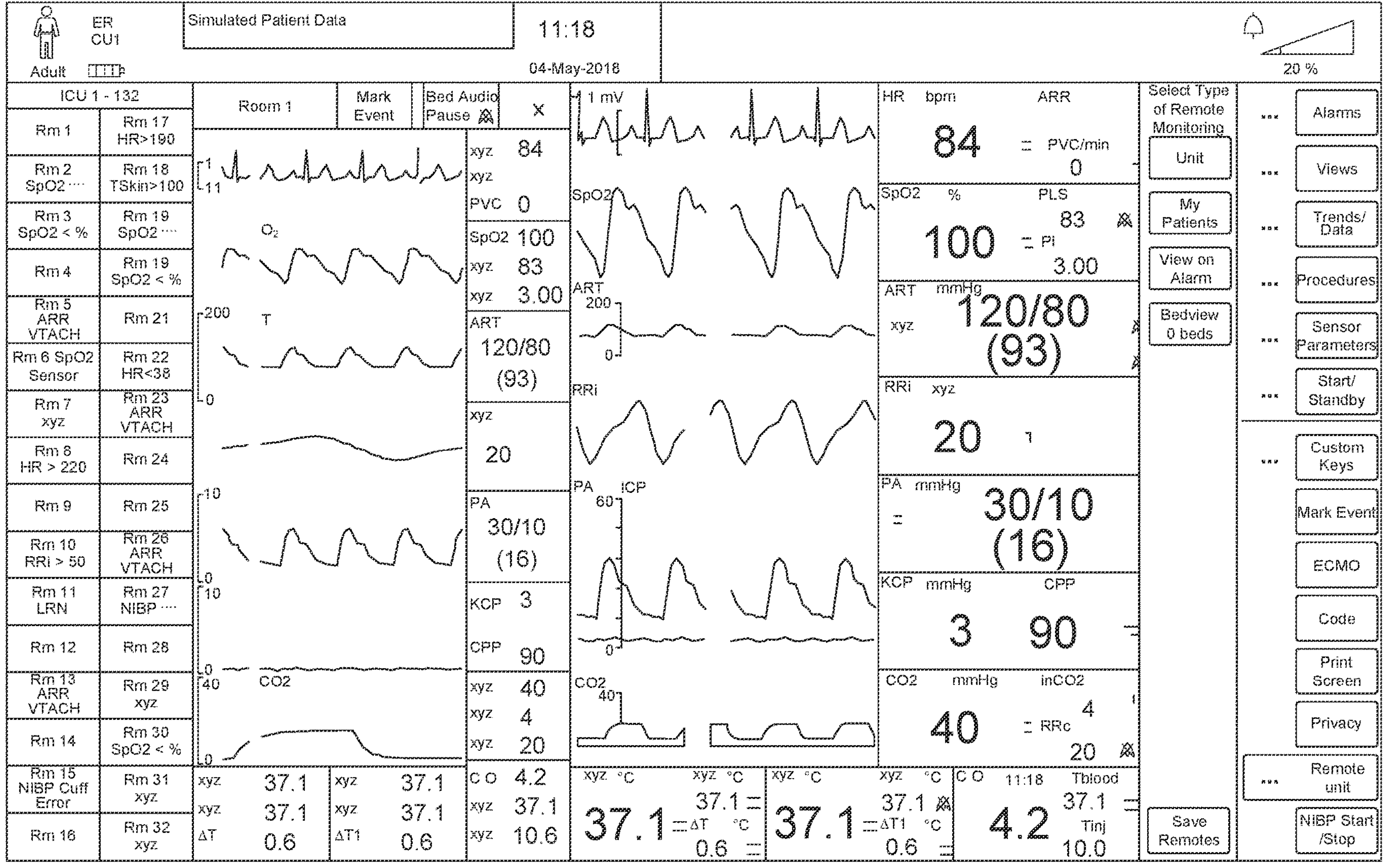
FIGS. 6A-6F show different display formats of local and remote views rendered on a display according to one or more embodiments.

FIG. 6A shows a signal bed remote view. Here, eight vertical channels could be used with each of the eight channels will be assigned to one remote patient. Each channel has a waveform and a parameter box except for channel 8 which has four parameter boxes. Thus, seven remote waveforms and eleven parameter boxes are shown.

Figure 6B:
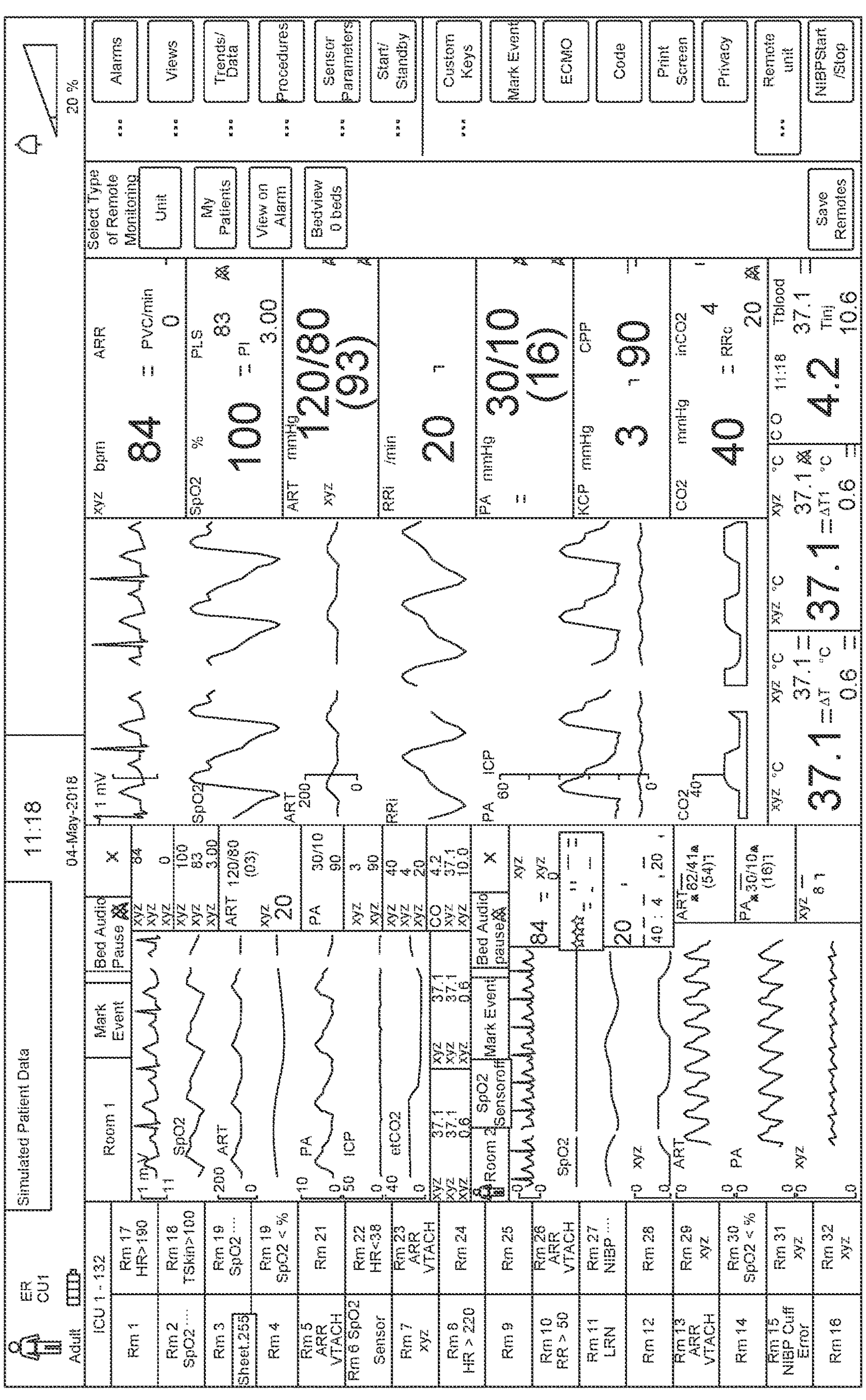

FIG. 6B shows a two bed remote view. In this remote view screen, there are 8 channels allocated to the first patient. The eighth channel is used for additional parameter boxes. The second 8 channels are allocated to the second patient. However, only 7 channels are populated.

Figure 6C:
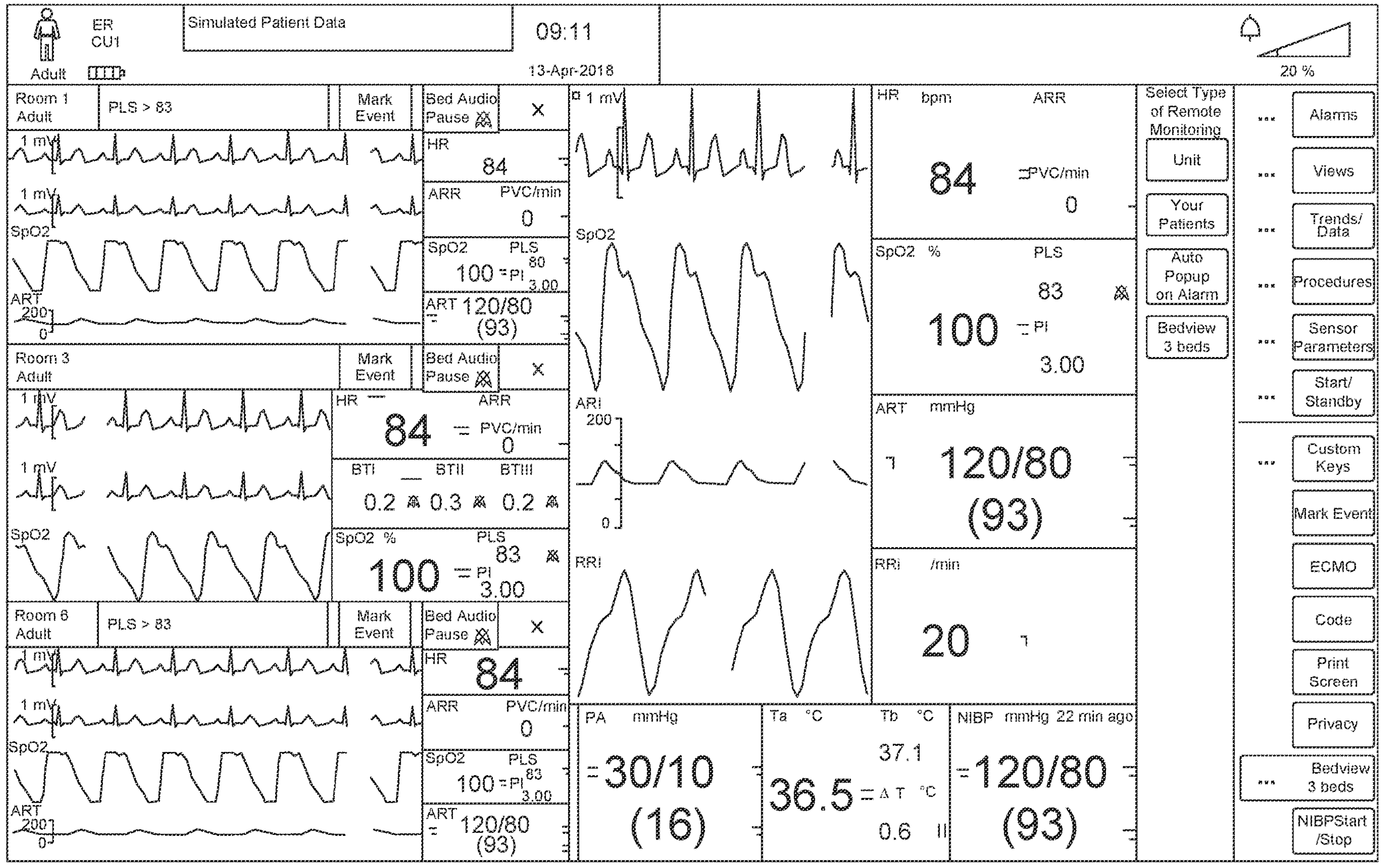

FIG. 6C shows a three bed remote view. In this remote view screen, 4 channels are allocated to the first patient, 3 channels are allocated to the second patient, and 4 channels are allocated to the third patient. Eleven channels are used in this format.

Figure 6D:
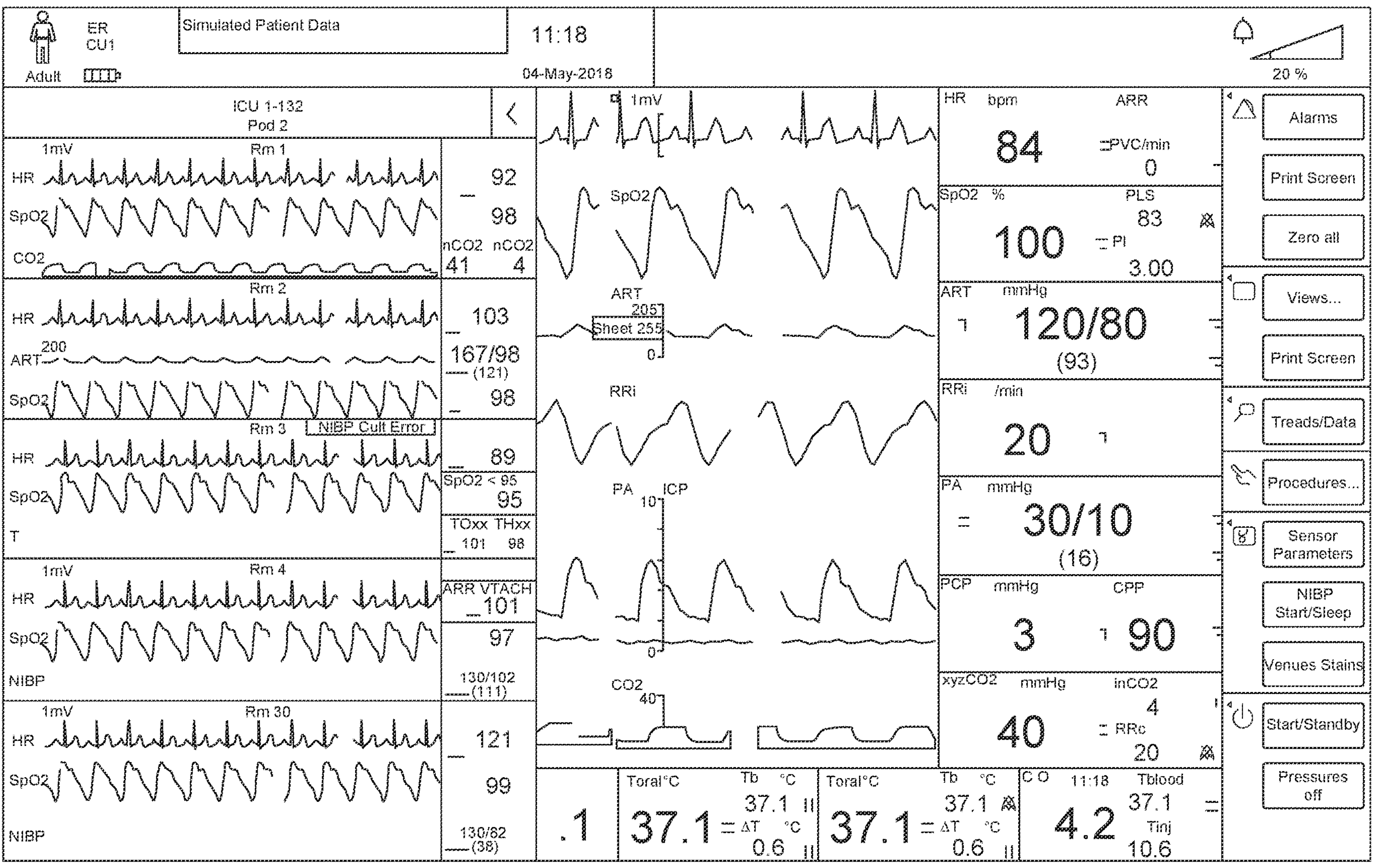

FIG. 6D shows a five bed remote view with three channels being allocated to each patient for a total of 15 allocated channels.

Figure 6E:
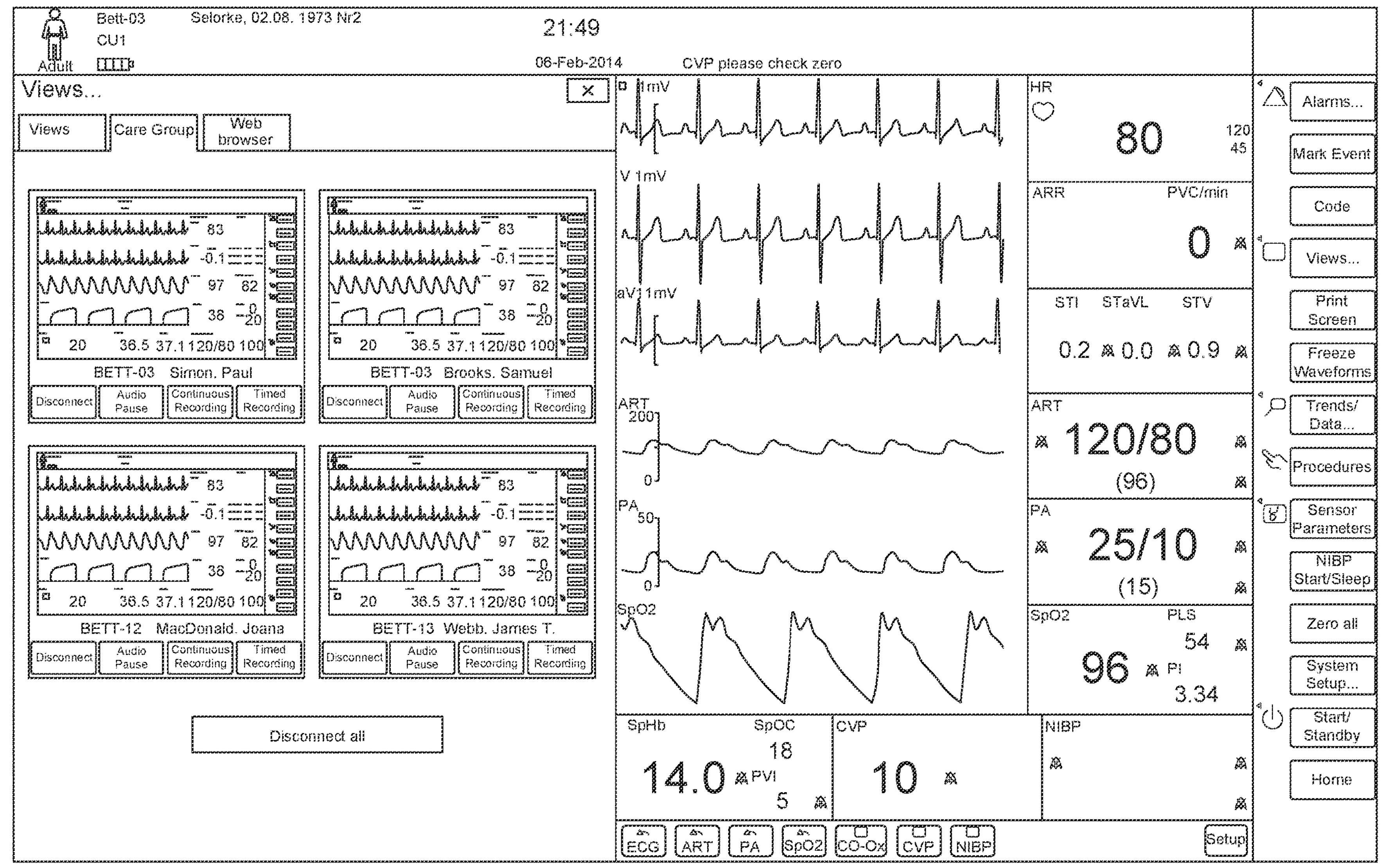

FIG. 6E shows a four bed remote view in a 4×4 mode. Four channels are allocated to each patient for a total of 16 allocated channels.

Figure 6F:
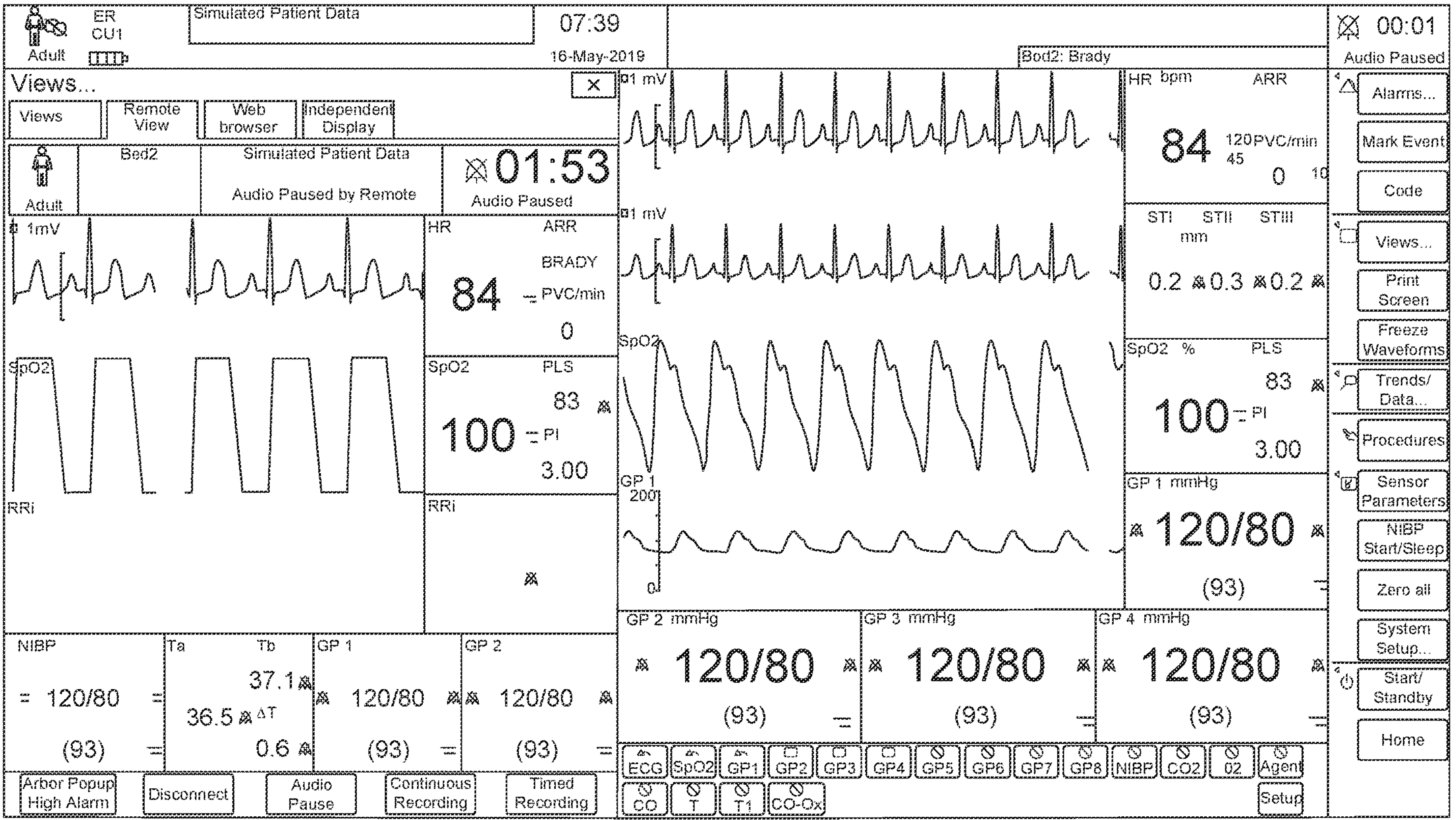

In FIG. 6F, only four channels are needed to render the remote view.

Historical data may be used by the remote view distribution device 100 to generate remote views. For example, historical data may refer to the last 5 seconds of data or some other time interval of data. When a remote view is rendered on a screen without historical data, one will see a single data point grow into a line that will continue to grow and slowly fill the screen in approximately 5 seconds. The other choice is to include historical data so that the entire waveform is seen as soon as the remote view is rendered. In this case, when the remote view is rendered on the screen you will see the past 5 seconds and it will slowly be replaced with real time data. Thus, either a waveform may be generated without historical data and the waveform populates the screen over time or a waveform includes its historical data so that the entire screen is populated with the waveform and its historical data. The remote view distribution device 100 is capable of generating remote view MDIBs that include or do not include historical data waveforms.

While various embodiments have been disclosed, it will be apparent to those skilled in the art that various changes and modifications can be made which will achieve some of the advantages of the concepts disclosed herein without departing from the spirit and scope of the present disclosure. It will be obvious to those reasonably skilled in the art that other components performing the same functions may be suitably substituted. It is to be understood that other embodiments may be utilized and structural or logical changes may be made without departing from the scope of the present disclosure. It should be mentioned that features explained with reference to a specific figure may be combined with features of other figures, even in those not explicitly mentioned. Such modifications to the general inventive concept are intended to be covered by the appended claims and their legal equivalents.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims—other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods. For example, the techniques described in this disclosure may be implemented, at least in part, in hardware, software, firmware, or any combination thereof. For example, various aspects of the described techniques may be implemented within one or more processors, including one or more microprocessors, DSPs, ASICs, or any other equivalent integrated or discrete logic circuitry, as well as any combinations of such components.

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. A remote view distribution device, comprising:

a multi-channel point-to-point service-oriented device connectivity (SDC) communication interface configured to be connected to a first physiological monitoring device and a second physiological monitoring device, to asynchronously receive first patient data of a first medical data information base (MDIB) from the first physiological monitoring device on a first channel and asynchronously receive second patient data of a second medical data information base (MDIB) from the second physiological monitoring device on a second channel, wherein the first patient data corresponds to a first patient and the second patient data corresponds to a second patient, and wherein the first MDIB comprises a plurality of first data objects and the second MDIB comprises a plurality of second data objects;

a medical data information base (MDIB) buffer to buffer the first MDIB that includes the first patient data received on the first channel and buffer the second MDIB that includes the second patient data received on the second channel; and a processing circuit to selectively extract at least one first data object of the first MDIB from the MDIB buffer based on remote view configuration information, generate a first remote view MDIB comprising the extracted at least one first data object, and transmit the first remote view MDIB to the second physiological monitoring device via the second channel of the multi-channel point-to-point SDC communication interface.

2. The remote view distribution device of claim 1, wherein the processing circuit is to synchronously selectively extract at least one second data object of the second MDIB from the MDIB buffer based on the remote view configuration information, generate a second remote view MDIB comprising the extracted at least one second data object, and transmit the second remote view MDIB to the first physiological monitoring device via the first channel of the multi-channel point-to-point SDC communication interface.

3. The remote view distribution device of claim 1, further comprising:

a synchronizer to synchronize extracting the at least one first data object of the first MDIB and the at least one second data object of the second MDIB from the MDIB buffer and to synchronize transmissions of the at least one first data object of the first MDIB and the at least one second data object of the second MDIB to the processing circuit.

4. The remote view distribution device of claim 1, wherein the remote view configuration information includes configuration information received from the first physiological monitoring device and configuration information received from the second physiological monitoring device.

5. The remote view distribution device of claim 1, further comprising:

wherein the multi-channel point-to-point SDC communication interface further asynchronously receives third patient data of a third medical data information base (MDIB) from a third physiological monitoring device on a third channel, wherein the third patient data corresponds to a third patient, and wherein the third MDIB comprises a plurality of third data objects;

wherein the MDIB buffer further buffers the third MDIB that includes the third patient data received on the third channel; and wherein the processing circuit further synchronously selectively extracts at least one third data object of the third MDIB from the MDIB buffer based on the remote view configuration information, generates the first remote view MDIB comprising the extracted at least one first data object and the extracted at least one third data object, and transmits the first remote view MDIB to the second physiological monitoring device via the second channel of the multi-channel point-to-point SDC communication interface.

6. The remote view distribution device of claim 1, further comprising:

wherein the multi-channel point-to-point SDC communication interface further asynchronously receives third patient data of a third medical data information base (MDIB) from a third physiological monitoring device on a third channel, wherein the third patient data corresponds to a third patient, and wherein the third MDIB comprises a plurality of third data objects;

wherein the MDIB buffer further buffers the third MDIB that includes the third patient data received on the third channel; and wherein the processing circuit further synchronously selectively extracts at least one third data object of the third MDIB from the MDIB buffer based on the remote view configuration information, generates a second remote view MDIB comprising the extracted at least one first data object, and transmits the second remote view MDIB to the third physiological monitoring device via the third channel of the multi-channel point-to-point SDC communication interface.

7. The remote view distribution device of claim 1, further comprising:

wherein the multi-channel point-to-point SDC communication interface further asynchronously receives third patient data of a third medical data information base (MDIB) from a third physiological monitoring device on a third channel, wherein the third patient data corresponds to a third patient, and wherein the third MDIB comprises a plurality of third data objects;

wherein the MDIB buffer further buffers the third MDIB that includes the third patient data received on the third channel; and wherein the processing circuit further selectively extracts a first data portion of the plurality of first data objects of the first MDIB from the first MDIB buffer based on the remote view configuration information for the first remote view MDIB, extracts a second data portion of the plurality of first data objects of the first MDIB from the first MDIB buffer based on the remote view configuration information for a second remote view MDIB, wherein the first and the second data portions are different data portions, generates the first remote view MDIB comprising the extracted first data portion, generates the second remote view MDIB comprising the extracted second data portion, transmits the first remote view MDIB to the second physiological monitoring device via the second SDC connection interface, and transmits the second remote view MDIB to the third physiological monitoring device via the third channel of the multi-channel point-to-point SDC communication interface.

8. The remote view distribution device of claim 1, wherein the first remote view MDIB enables the second physiological monitoring device to render a remote view on a display.

9. A remote view distribution device, comprising:

a point-to-point service-oriented device connectivity (SDC) communication interface including a plurality of channels each configured to be coupled to a respective physiological monitoring device of a plurality of physiological monitoring devices for asynchronously receiving patient data from each of the plurality of physiological monitoring devices;

a medical data information base (MDIB) buffer to buffer the patient data, received on a respective channel of the point-to-point SDC communication interface from each of the plurality of physiological monitoring devices, as a respective plurality of MDIBs, wherein each corresponding MDIB comprises a plurality of data objects; and a processing circuit to:

generate a remote view MDIB based on remote view configuration information, including synchronously selectively extracting at least one data object from one or more of the plurality of MDIBs, and transmit the remote view MDIB to at least one physiological monitoring device of the plurality of physiological monitoring devices via a respective one or more of the plurality of channels of the point-to-point SDC communication interface based on the remote view configuration information.

10. The remote view distribution device of claim 9, wherein the remote view configuration information identifies the at least one data object to be extracted from the one or more of the plurality of MDIBs and identifies the at least one physiological monitoring device to which the remote view MDIB is to be transmitted.

11. The remote view distribution device of claim 9, further comprising:

a synchronizer to synchronize extracting the at least one data object of the plurality of MDIBs from the MDIB buffer and synchronize transmissions of the at least one data object of the plurality of MDIBs to the processing circuit.

12. The remote view distribution device of claim 9, wherein the remote view MDIB enables the at least one physiological monitoring device to render a remote view on a display.

13. A remote view distribution system, comprising:

a plurality of physiological monitoring devices, each configured to monitor one or more physiological parameters of a respective patient and each comprising a display to display a local view of one or more physiological parameters of its respective patient and a remote view of one or more physiological parameters of at least one remote patient;

a remote view distribution device comprising:

a point-to-point service-oriented device connectivity (SDC) communication interface including a plurality of channels, wherein each of the plurality of channels is configured to receive patient data from a respective different one of a plurality of physiological monitoring devices;

a medical data information base (MDIB) buffer to buffer a plurality of MDIBs, wherein each MDIB includes the patient data from the respective physiological monitoring device on the respective channel of the point-to-point SDC communication interface, and wherein each MDIB comprises a plurality of data objects; and a processing circuit to:

generate a remote view MDIB based on remote view configuration information, including selectively extracting at least one data object from the plurality of MDIBs, and transmit the remote view MDIB to at least one physiological monitoring device of the plurality of physiological monitoring devices via a respective channel of the point-to-point SDC communication interface based on the remote view configuration information.

14. The remote view distribution system of claim 13, wherein the remote view configuration information identifies the at least one data object to be extracted from the plurality of MDIBs and identifies the at least one physiological monitoring device to which the remote view MDIB is to be transmitted.

15. The remote view distribution system of claim 13, further comprising:

a synchronizer to synchronize extracting the at least one data object of the plurality of MDIBs from the MDIB buffer and synchronize transmissions of the at least one data object of the plurality of MDIBs to the processing circuit.

16. The remote view distribution system of claim 13, wherein the remote view MDIB enables the at least one physiological monitoring device to render a respective remote view on its display.

17. The remote view distribution system of claim 13, further comprising:

a data source to provide additional patient information with respect a patient, wherein the processing circuit receives the additional patient information and inserts the additional patient information into the remote view MDIB.

18. The remote view distribution system of claim 17, wherein the data source is a camera and the additional patient information is a video stream of the patient.

* * * * *